US012691136B2

(12) United States Patent
Yan et al.

(10) Patent No.: US 12,691,136 B2
(45) Date of Patent: Jul. 28, 2026

(54) METAL COMPOSITIONS AND METHODS OF USE THEREOF

(71) Applicant: THE UNIVERSITY OF MASSACHUSETTS, Boston, MA (US)

(72) Inventors: Mingdi Yan, Bedford, MA (US); William Ndugire, Lowell, MA (US); Olof Ramstrom, Lowell, MA (US); N. G. Hasitha Raviranga, Lowell, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 678 days.

(21) Appl. No.: 17/997,493

(22) PCT Filed: Apr. 29, 2021

(86) PCT No.: PCT/US2021/029859

§ 371 (c)(1),
(2) Date: Oct. 28, 2022

(87) PCT Pub. No.: WO2021/222541

PCT Pub. Date: Nov. 4, 2021

(65) Prior Publication Data

US 2023/0201246 A1 Jun. 29, 2023

Related U.S. Application Data

(60) Provisional application No. 63/017,308, filed on Apr. 29, 2020.

(51) Int. Cl.

| | |
|---|---|
| ***A61K 31/7135*** | (2006.01) |
| ***A61K 33/242*** | (2019.01) |
| ***A61K 45/06*** | (2006.01) |
| ***A61K 47/20*** | (2006.01) |
| ***A61P 31/04*** | (2006.01) |

(52) U.S. Cl.

CPC ........ *A61K 31/7135* (2013.01); *A61K 33/242* (2019.01); *A61K 45/06* (2013.01); *A61K 47/20* (2013.01); *A61P 31/04* (2018.01)

(58) Field of Classification Search

CPC .. A61K 31/7135; A61K 33/242; A61K 45/06; A61K 47/20; A61P 31/04

See application file for complete search history.

(56) References Cited

U.S. PATENT DOCUMENTS

| | | | | |
|---|---|---|---|---|
| 8,518,172 | B2 * | 8/2013 | Morizane ............... | C09D 5/106 106/286.6 |
| 2011/0053880 | A1 * | 3/2011 | Fussenegger ...... | A61K 31/4409 514/357 |
| 2011/0206747 | A1 | 8/2011 | Lagny et al. | |

FOREIGN PATENT DOCUMENTS

WO WO-2016123368 A1 * 8/2016

OTHER PUBLICATIONS

Nishida, Clinton R., and Paul R. Ortiz de Montellano. "Bioactivation of antituberculosis thioamide and thiourea prodrugs by bacterial and mammalian flavin monooxygenases." Chemico-Biological Interactions 192.1-2 (2011): 21-25. (Year: 2011).*

Henderson, W. et al., Synthesis, characterisation, supramolecular aggregation and biological activity of phosphine gold (1) complexes with monoanionic thiourea ligands, Inorganica Chimica Acta, vol. 359, Issue 1, 2006, pp. 204-214, ISSN 0020-1693, https://doi.org/10.1016/j.ica.2005.07.046.

International Search Report and Written Opinion for PCT/US2021/029859, Dated Jul. 13, 2021.

* cited by examiner

*Primary Examiner* — Scarlett Y Goon
*Assistant Examiner* — David H Cho
(74) *Attorney, Agent, or Firm* — CANTOR COLBURN LLP

(57) ABSTRACT

Compositions comprising metal entities in combination with an activating agent, or pharmaceutically acceptable salts thereof are disclosed. Certain compositions are active as antibacterial, antiviral, antifungal, anti-protozoal, and/or anti-worm agents. The disclosure provides pharmaceutical compositions containing the compositions. Methods of using the composition to treat bacterial infections are disclosed.

17 Claims, 5 Drawing Sheets

METAL COMPOSITIONS AND METHODS OF USE THEREOF

CROSS-REFERENCE TO RELATED APPLICATION

This application is a National Stage Entry of PCT/US2021/029859, filed Apr. 29, 2021, and published as WO 2021/222541 A1, which claims priority to and the benefit of U.S. Provisional Application No. 63/017,308, filed on Apr. 29, 2020, each of which is incorporated by reference herein its entirety.

STATEMENT OF GOVERNMENTAL INTEREST

The National Institutes of Health funded the subject matter of this disclosure. The United States Government has certain rights in this application.

BACKGROUND

The increasing prevalence of resistance to the majority of existing antibiotics has generated a pressing global healthcare crisis. To undermine the actions of antibiotics, bacteria have developed powerful resistance mechanisms including mutational alteration of the targeted proteins, under-expression of membrane porins, expression of enzymes that degrade antibiotics, and overexpression of efflux pumps that drive antibiotics out of the bacterium. Certain highly resistant bacteria have acquired multiple mechanisms against most available antibiotics. The situation is especially dire for gram-negative bacteria. The recent addition of antibiotics in the clinical pipeline has been limited to treating gram-positive infections, and there has been no new class of clinically-approved antibiotics for gram-negative bacteria since the discovery of quinolones in 1968. Untreatable antimicrobial resistance (AMR) is rapidly emerging in, for example, *Escherichia coli, Klebsiella pneumoniae, Pseudomonas aeruginosa* and *Acinetobacter baumannii* that are resistant to all commonly used antibiotics, including fluoroquinolones, β-lactams, macrolides, aminoglycosides, tetracyclines, and the last-resort antibiotic colistin, contributing to the majority of deaths caused by hospital-acquired infections. There is therefore an urgent need to develop novel antibiotics.

SUMMARY

The disclosure includes a composition comprising a metal entity and an activating agent.

The disclosure includes methods of treating a bacterial infection in a patient comprising administering a therapeutically effective amount of a composition comprising a metal entity and an activating agent.

The disclosure includes methods of inhibiting the growth of a bacterium in vitro or in vivo comprising contacting a bacterium with a composition comprising a metal entity and an activating agent.

The disclosure includes methods of treating a biofilm infection in a patient comprising administering a therapeutically effective amount of a composition comprising a metal entity and an activating agent.

The disclosure includes methods of inhibiting the growth of a biofilm in vitro or in vivo comprising contacting a biofilm with a composition comprising a metal entity and an activating agent.

The disclosure includes methods of treating a parasitic infection in a patient comprising administering a therapeutically effective amount of a composition comprising a metal entity and an activating agent.

The disclosure includes methods of inhibiting the growth of a parasite in vitro or in vivo comprising contacting a parasite with a composition comprising a metal entity and an activating agent.

The disclosure includes methods of treating a fungal infection in a patient comprising administering a therapeutically effective amount of a composition comprising a metal entity and an activating agent.

The disclosure includes methods of inhibiting the growth of a fungus in vitro or in vivo comprising contacting a fungus with a composition comprising a metal entity and an activating agent.

The disclosure includes methods of treating a viral infection in a patient comprising administering a therapeutically effective amount of a composition comprising a metal entity and an activating agent.

The disclosure includes methods of inhibiting the growth of a virus in vitro or in vivo comprising contacting a virus with a composition comprising a metal entity and an activating agent.

The disclosure includes methods of treating a protozoan infection in a patient comprising administering a therapeutically effective amount of a composition comprising a metal entity and an activating agent.

The disclosure includes methods of inhibiting the growth of a protozoan in vitro or in vivo comprising contacting a protozoan with a composition comprising a metal entity and an activating agent.

The disclosure includes methods of treating a worm infection in a patient comprising administering a therapeutically effective amount of a composition comprising a metal entity and an activating agent.

The disclosure includes methods of inhibiting the growth of a worm in vitro or in vivo comprising contacting a worm with a composition comprising a metal entity and an activating agent.

The disclosure includes pharmaceutical compositions comprising a composition comprising a metal entity and an activating agent.

BRIEF DESCRIPTION OF THE DRAWINGS

FIG. 1A shows a drastic decrease in minimal inhibitory concentration (MIC, μM [Au]) of the gold entity—1.8 nm gold nanoclusters protected with D-maltose ($Au_{101}$Mal), 13 nm gold nanoparticles protected with citrate ligands (AuNP-citrate), or 1.8 nm gold nanoclusters protected with D-trehalose ($Au_{101}$Tre)—against *P. aeruginosa* PAO1 with the addition of TU. FIG. 1B shows that almost no change in activity (MIC) was observed for piperacillin, gentamicin, or ciprofloxacin with the addition of TU. The Au concentration in each gold entity was quantitated by ICP-MS (inductively coupled plasma mass spectrometry).

DETAILED DESCRIPTION

Chemical Description and Terminology

Figure 1A:
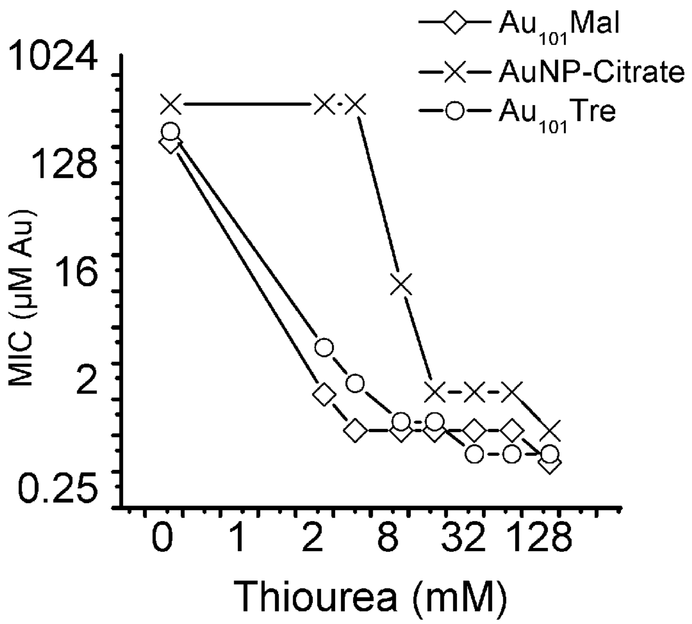
FIGS. 1A-1B show isobolograms of compounds in combination with thiourea (TU).

Prior to setting forth the invention in detail, it may be helpful to provide definitions of certain terms to be used in this disclosure. Compounds are described using standard nomenclature. Unless defined otherwise, all technical and scientific terms used herein have the same meaning as is commonly understood by one of skill in the art to which this invention belongs. Unless clearly contraindicated by the context, each compound name includes the free acid or free base form of the compound as well as all pharmaceutically acceptable salts of the compound. Each compound name also includes all isotopes of the included atoms.

A dash ("-") that is not between two letters or symbols is used to indicate a point of attachment for a substituent. For example, —(C═O)OH is attached through the carbon atom of the keto (C═O) group.

The terms "a" and "an" do not denote a limitation of quantity, but rather denote the presence of at least one of the referenced items. The term "or" means "and/or". The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in any suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

"Alkyl" is a branched or straight chain saturated aliphatic hydrocarbon group, having the specified number of carbon atoms, generally from 1 to about 8 carbon atoms. Examples of alkyl include, but are not limited to, methyl, ethyl, n-propyl, isopropyl, n-butyl, 3-methylbutyl, t-butyl, n-pentyl, and sec-pentyl.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Cycloalkyl" is a saturated hydrocarbon ring group, having the specified number of carbon atoms. Monocyclic cycloalkyl groups typically have from 3 to about 8 (e.g., 3, 4, 5, 6, 7, or 8) carbon ring atoms. Cycloalkyl substituents may be pendant from a substituted boron, carbon, nitrogen, oxygen, silicon, phosphorus, sulfur, or selenium atom, or a substituted carbon atom that may have two substituents, or may have a cycloalkyl group, which is attached as a spiro group. Examples of cycloalkyl groups include cyclopropyl, cyclobutyl, cyclopentyl, or cyclohexyl as well as bridged or caged saturated ring groups such as norbornane or adamantane.

"Halo" or "halogen" indicates any of fluoro, chloro, bromo, and iodo.

"Aryl" indicates an aromatic ring, for example, phenyl or pyridinyl, or a fused aromatic ring system, for example, naphthyl or indolyl.

As used herein, the term "hydrocarbyl", whether used by itself, or as a prefix, suffix, or fragment of another term, refers to a residue that contains only carbon and hydrogen. The residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. However, when the hydrocarbyl residue is described as substituted, it may, optionally, contain heteroatoms over and above the carbon and hydrogen members of the substituent residue. Thus, when specifically described as substituted, the hydrocarbyl residue can also contain one or more carbonyl groups, amino groups, hydroxyl groups, or the like.

As used herein, the term "heterohydrocarbyl", whether used by itself, or as a prefix, suffix, or fragment of another term, refers to a residue that contains carbon, hydrogen, and at least one heteroatom. The residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated moieties.

Unless substituents are otherwise specifically indicated, each of the foregoing groups can be unsubstituted or substituted, provided that the substitution does not significantly or adversely affect synthesis, stability, or use of the compound. "Substituted" means that the compound, group, or atom is substituted with at least one (e.g., 1, 2, 3, or 4)

substituent instead of hydrogen, where each substituent is independently groups, including, but not limited to, nitro ($—NO_2$), primary amino ($—NH_2$), secondary amino (—NHR), tertiary amino ($—NR_2$), ammonium ($—NR_3^+$), phosphino ($—PR_2$), phosphonium ($—PR_3^+$), cyano (—CN), hydroxy (—OH), halogen, thiol (—SH), thioalkyl (—SR), thioaryl, thiocyano (—SCN), $C_{1-6}$ alkyl, $C_{2-6}$ alkenyl, $C_{2-6}$ alkynyl, $C_{1-6}$ haloalkyl, $C_{1-9}$ alkoxy, $C_{1-6}$ haloalkoxy, $C_{3-12}$ cycloalkyl, $C_{5-18}$ cycloalkenyl, $C_{6-12}$ aryl, $C_{7-13}$ arylalkylene (e.g., benzyl), $C_{7-12}$ alkylarylene (e.g., toluyl), $C_{4-12}$ heterocycloalkyl, $C_{3-12}$ heteroaryl, $C_{1-6}$ alkyl sulfonyl ($—S(=O)_2$-alkyl), or $C_{6-12}$ arylsulfonyl ($—S(=O)_2$-aryl), provided that the substituted atom's normal valence is not exceeded, and that the substitution does not significantly or adversely affect the manufacture, stability, or desired property of the compound. A stable compound or stable structure is meant to imply a compound that is sufficiently robust to survive isolation from a reaction mixture, and subsequent formulation into an effective therapeutic agent.

"Pharmaceutical compositions" are compositions comprising at least one metal entity and activating agent, and at least one other substance, such as a carrier. Pharmaceutical compositions optionally contain one or more additional active agents. When specified, pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, nontoxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues, such as carboxylic acids; and the like. The pharmaceutically acceptable salts include the conventional nontoxic salts and the quaternary ammonium salts of the parent compound formed, for example, from nontoxic inorganic or organic acids. For example, conventional nontoxic acid salts include those derived from inorganic acids, such as hydrochloric, hydrobromic, sulfuric, sulfamic, phosphoric, nitric, and the like; and the salts prepared from organic acids, such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethanedisulfonic, oxalic, isethionic, $HOOC—(CH_2)_n—COOH$ where n is 0-4, and the like.

The term "carrier" applied to pharmaceutical compositions/combinations of the present disclosure refers to a diluent, excipient, or vehicle with which an active compound is provided. To be pharmaceutically acceptable a carrier must be safe, nontoxic and neither biologically nor otherwise undesirable.

A "patient" is a human or nonhuman animal in need of medical treatment. Medical treatment can include treatment of an existing condition, such as a disease or disorder, prophylactic or preventative treatment, or diagnostic treatment. In certain embodiments disclosed herein "medical treatment" means treatment of a diagnosed cancer or known tumor. In certain embodiments the patient is a human patient.

"Treatment," as used herein includes providing a compound or salt, either as the only active agent or together with an additional active agent sufficient to: (a) prevent or decrease the likelihood a disease or a symptom of a disease from occurring in a patient who may be predisposed to the disease but has not yet been diagnosed as having it; (b) inhibiting the disease, (i.e., arresting its development); and (c) relieving the disease, (i.e., causing a remission of the disease).

A "therapeutically effective amount" of a pharmaceutical composition/combination of this disclosure means an amount effective, when administered to a patient, to provide a therapeutic benefit such as an amelioration of symptoms, for example, an amount effective to decrease the symptoms of a bacterial, fungal or parasitic infection.

Chemical Description

The inventors hereof have discovered that compositions, comprising a metal entity, for example, a gold entity or its pharmaceutically acceptable salt form, and an activating agent comprising, for example, a thiourea or its derivative, are highly potent against drug-resistant gram-negative or gram-positive bacteria, or mycobacteria. Some gold-thiourea complexes have demonstrated antibacterial activity against gram-positive strains such as *Bacillus subtilis* (Henderson et al., Synthesis, characterisation, supramolecular aggregation and biological activity of phosphine gold(I) complexes with monoanionic thiourea ligands. *Inorg. Chim. Acta* 2006, 359 (1), 204-214). In such compounds, the thiourea group is covalently bound to the gold entity. Therefore, it was a surprising and unexpected result for a composition comprising the combination of a metal entity and an activating agent such as thiourea to have antibacterial activity in gram-negative strains.

The activating agent can include thiourea or a derivative thereof, a thiocarbamate, a thiocarbonate, a xanthate, a thiocarbohydrazide, a thiosemicarbazide, a thioamide, a thiosulfate, a sulfite, a thiocyanate, a carbene, a cyanide, glycine, a nitrene, tautomers thereof, or a combination thereof.

The activating agent can include thiourea. Historically, thiourea was used in the treatment of hyperthyroidism at dosages up to 3 g/day before being discontinued due to the introduction of more effective therapies. In addition, in dosing studies in mice, several $LD_{50}$ values have been reported that cover ranges from 1000 mg/kg, 1750 mg/kg and 6200-6300 mg/kg while for comparison, the antibiotic chloramphenicol has an estimated oral mouse $LD_{50}$ of 1250 mg/kg.

Thiourea is also used at high concentrations (2 M) as a peroxide radical scavenger and in cell lysis buffers to enhance protein stability. Further, low doses are generally considered safe.

Thiourea has coordinating ability to metal entities, such as Au, through both the amino and thiol groups through tautomerism. For example, thiourea is known for its strong binding to gold. Therefore, the high reactivity of thiourea can activate otherwise nontoxic gold entities through the formation of active gold-thiourea compounds in vitro and in vivo.

The activating agent can include a thiourea derivative of AA-1 to AA-12.

AA-1

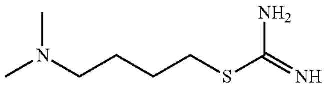

AA-2

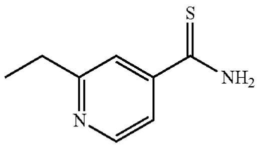

AA-3

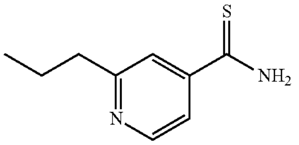

AA-4

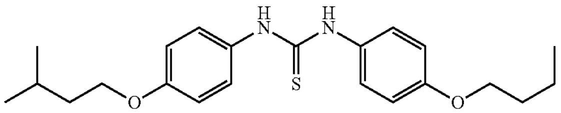

AA-5

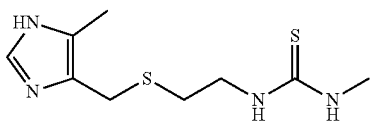

AA-6

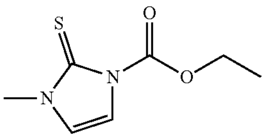

AA-7

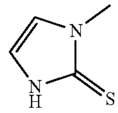

AA-8

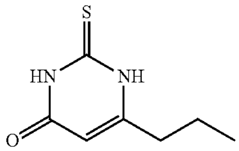

AA-9

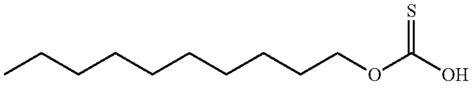

AA-10

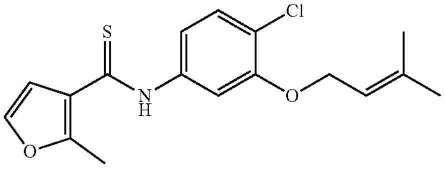

-continued

AA-11

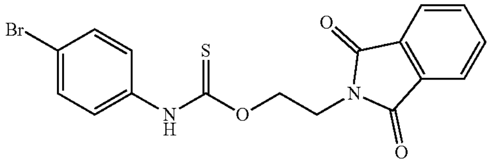

AA-12

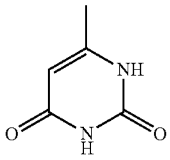

AA-1 to AA-12 are known therapeutic agents. AA-1 is a histamine N-methyltransferase inhibitor. AA-2 (ethionamide) is a second-line anti-tubercular agent that inhibits mycolic acid synthesis. It also may be used for treatment of leprosy. AA-3 (referred to as protionamide or prothionamide) is a drug used in the treatment of tuberculosis. AA-4 (referred to as thiocarlide, or isoxyl) is a thiourea drug used in the treatment of tuberculosis, inhibiting synthesis of oleic acid and tuberculostearic acid. AA-5 (referred to as metiamide) is a histamine H2 receptor antagonist developed from another H2 antagonist, burimamide. AA-6 to AA-8, referred to as thiamazole, carbamazole, and propylthiouracil, respectively, are FDA approved treatments for hyperthyroidism. AA-9 potentially targets the 3-oxoacyl-[acyl-carrier-protein] synthase of *Mycobacterium tuberculosis*. AA-10 (also referred to as UC-781) is a thiocarboxanilide non-nucleoside reverse transcriptase inhibitor (NNRTI). It is a topical microbicide targeted against the HIV. AA-11 is a non-nucleoside HIV-1 reverse transcriptase inhibitor. AA-12 is used for hyperthyroidism treatment in Europe, however it is not used clinically in the United States.

The compositions include a metal entity or pharmaceutically acceptable salt thereof. The metal entity can include a single metal, an alloy, or a combination thereof. The metal entity can include a transition metal, a post-transition metal, a metalloid, or a combination thereof. In some embodiments, the metal entity includes Au, Ag, Cu, Fe, Pt, Ti, Zn, Ga, In, Bi, or a combination thereof. Non-limiting examples of alloys such as heterobimetallic entities include Au—Ag, Au—Cu, Ag—Cu and the like. A non-limiting example of a heterotrimetallic entity includes Au—Ag—Cu. In some embodiments, the metal entity includes Au(I). In some embodiments, the metal entity includes Au(III).

The metal entity can include a metal compound, a metal nanocluster having an average diameter of up to 3 nm, a metal particle having an average diameter of greater than 3 nm, or a combination thereof. The average diameter can be determined by electron microscopy, force microscopy, or light scattering.

The metal entities can have a formula of $M_m(R)_r(W)_w(X)_x(Y)_y(Z)_z$ wherein: M is a transition metal, a post-transition metal, a metalloid, and can include a single metal, or a combination of more than one metal (e.g., an alloy); W is a thiol or a derivative thereof excluding carbohydrates; X is a phosphine or a derivative thereof; Y is a carbohydrate or a derivative thereof; Z is an anion; R is a ligand different than the W, X, Y, and Z, m is at least 1; r, w, x, y, and z are each independently 0 or at least 1; and at least one of r, w, x, y, and z is at least 1.

The metal entity can include a metal compound. The metal compound can have a formula of $M_m(R)_r(W)_w(X)_x(Y)_y(Z)_z$, wherein m is 1-3; r, w, x, y, and z are each independently 0-12; and at least one of r, w, x, y, and z is at least 1. The metal compound can include a therapeutic metal compound, including myochrysine, auranofin, sodium aurothiomalate, anochysine, allochrysine, solganol, aurothioglucose, or a combination thereof. The metal compound can include a combination of a metal compound having a formula of $M_m(R)_r(W)_w(X)_x(Y)_y(Z)_z$, wherein m is 1-3; r, w, x, y, and z are each independently 0-12; and at least one of r, w, x, y, and z is at least 1; and at least one of the foregoing therapeutic metal compounds.

In some aspects, the metal entity is a metal compound comprising gold. Exemplary gold compounds include:

1

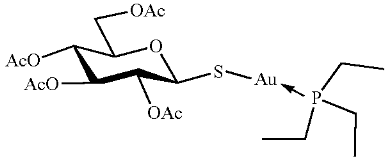

2

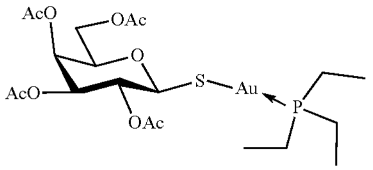

3

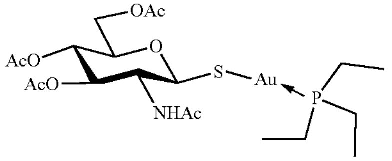

4

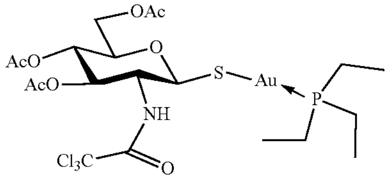

5

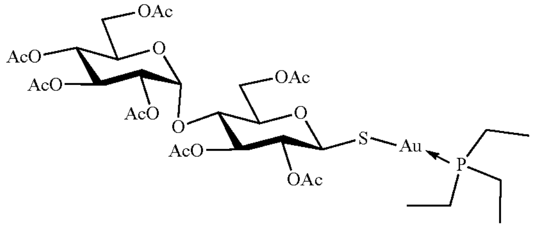

6

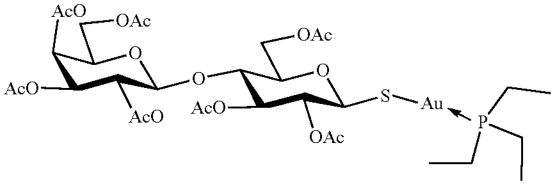

-continued

7

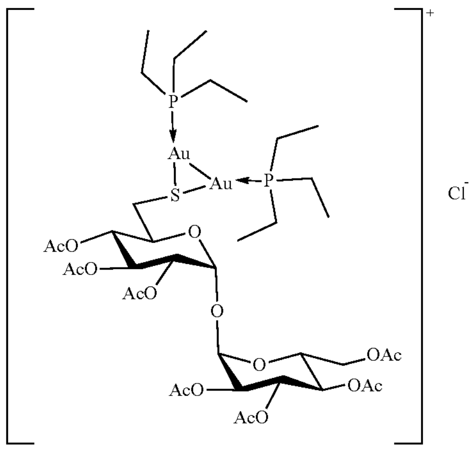

8

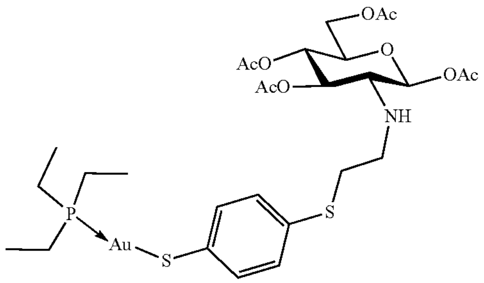

9

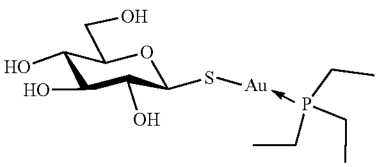

10

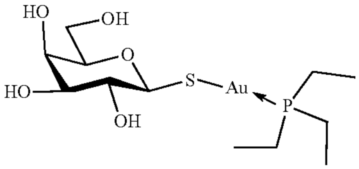

11

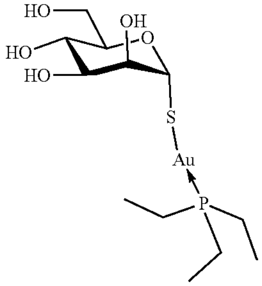

12

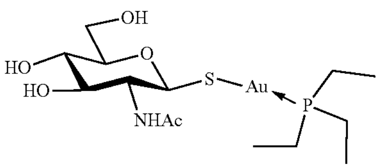

-continued
13
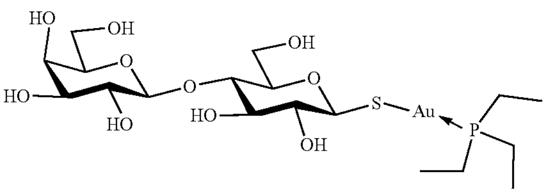
14
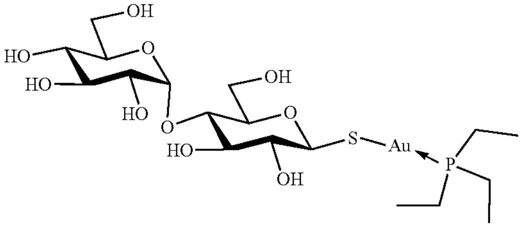
15
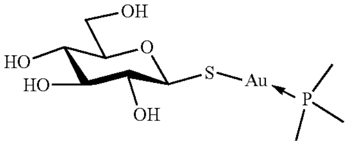
16
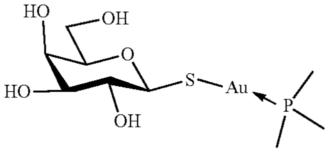
17
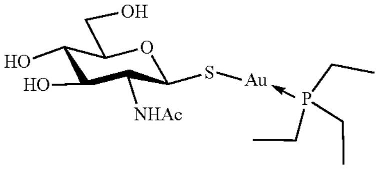
18
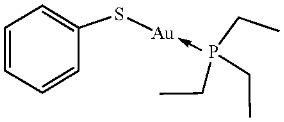
19
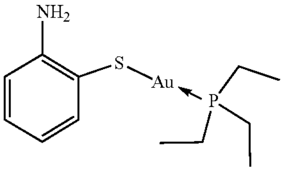
20
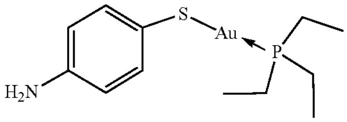
21
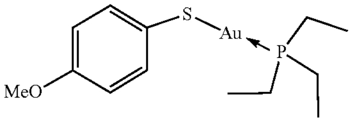
-continued
22
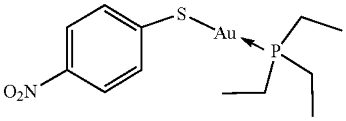
23
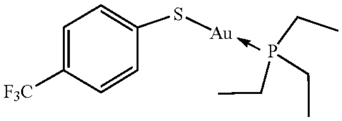
24
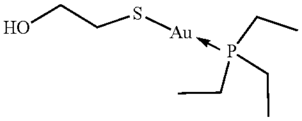
25
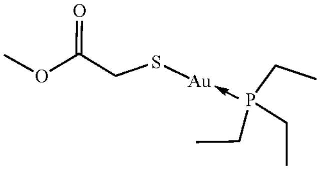
26
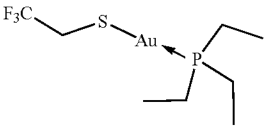
27
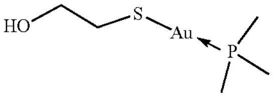
28
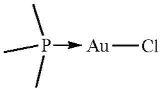
29
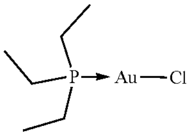
30
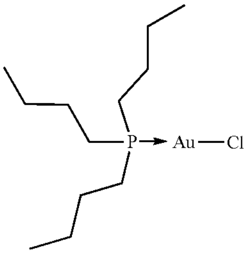
31
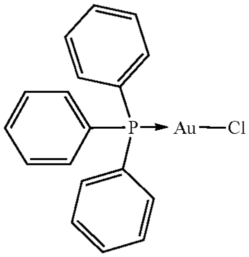

-continued
32
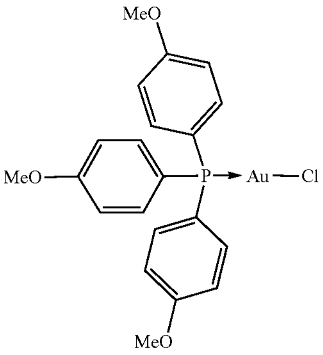
33
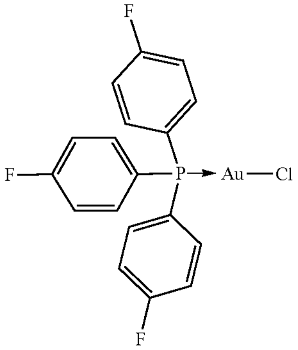
34
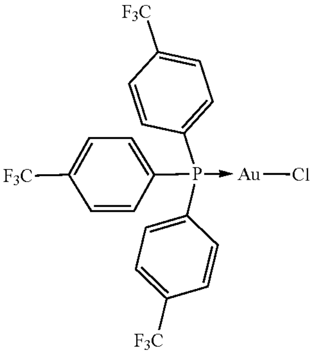
35
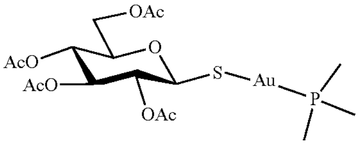
36
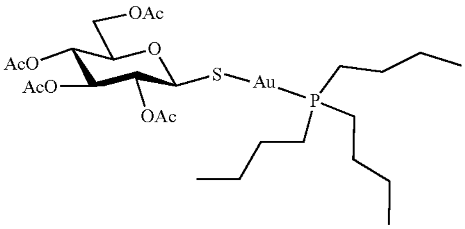
-continued
37
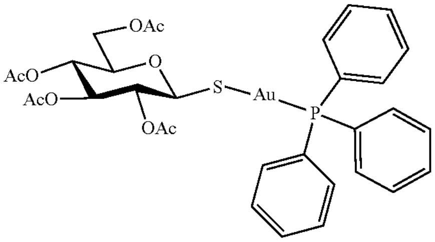
38
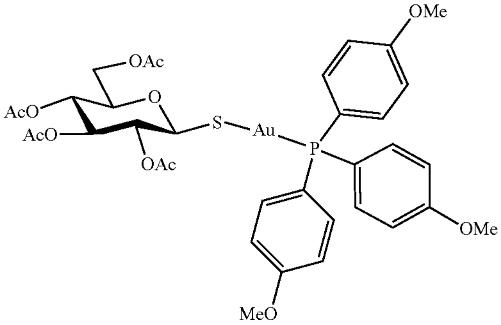
39
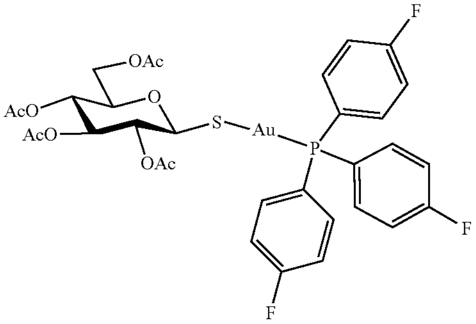
40
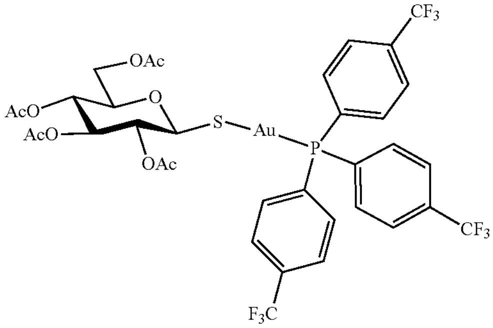
41
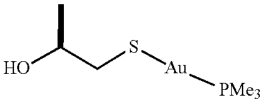
42
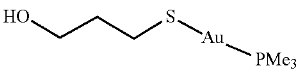
43
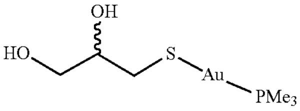

-continued

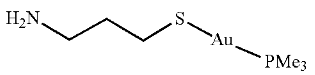

44

45

$Au(PMe)_3PF_6$ or a combination thereof.

The metal entity can include a metal nanocluster having an average diameter of up to 3 nm. The metal nanocluster can have the formula $M_m(R)_r(W)_w(X)_x(Y)_y(Z)_z$ wherein m is at least 4. In some embodiments, the metal nanocluster includes gold nanoclusters including $Au_{101}(TPPMS)_{21}Cl_5$, $Au_{101}(TPPMS)_{19}(Ac_4Glc\text{-}S)_2Cl_5$, $Au_{101}(TPPMS)_{14}(Ac_4Glc\text{-}S)_7Cl_5$, $Au_{101}(TPPMS)_{11}(Ac_4Glc\text{-}S)_{10}Cl_5$, and $Au_{101}(TPPMS)_7(Ac_4Glc\text{-}S)_{14}Cl_5$, $Au_{101}(Mal)_yCl_z$, $Au_{101}(Glc)_yCl_z$, $Au_{101}(Tre)_yCl_z$, $[Au_9(TPPMS)_8]Cl_3$, $[Au_{11}(PPh_3)_8Cl_2]Cl$, $Au_{25}(SG)_{18}$, $Au_{22}(SG)_{18}$, $Au_{18}(SG)_{14}$, or a combination thereof. In the foregoing, the designation "G" (e.g., $Au_{25}(SG)_{18}$, $Au_{22}(SG)_{18}$, $Au_{18}(SG)_{14}$) represents glutathione. In some aspects, the metal nanoclusters are alloy nanoclusters containing more than one metal, including bimetallic alloy nanoclusters (Au—Ag, Au—Ga, Au—Cu, and the like.) or trimetallic alloy nanoparticles (Au—Ag—Cu, Au—Cu—Ga, and the like).

In some aspects, the metal entity includes a metal particle having an average diameter of greater than 3 nm. The metal particle can include a microparticle or a nanoparticle. The metal particle can have the formula $M_m(R)_r(W)_w(X)_x(Y)_y(Z)_z$ wherein m is at least 4. The metal particles can include a particle comprising a single metal or an alloy particle. The metal particles can include a ligand-protected particle. The metal particle can include a carbohydrate-protected particle, a thiourea-protected particle, a citrate-protected particle, a glutathione-protected particle, a catechol-protected particle, a zwitterion-protected particle, a glycol-protected particle, a lactic acid-protected particle, a glycolic acid-protected particle, an amino acid-protected particle, a peptide-protected particle, a protein-protected particle, an amine-protected particle, an alkyne-protected particle, or a combination thereof.

Referring to $M_m(R)_r(W)_w(X)_x(Y)_y(Z)_z$, the R group, the W group, the X group, the Y group, the Z group, or a combination thereof render the metal entity biocompatible. As used herein, "biocompatible" means non-toxic or having low toxicity in human cells.

The R group in the formula $M_m(R)_r(W)_w(X)_x(Y)_y(Z)_z$ is a ligand different than the W, X, Y, and Z groups. The R group can be monomeric, oligomeric, or polymeric. In some aspects, R is derived from thiourea or a derivative thereof, a cyclic thiourea derivative (e.g., thiamazole, propylthiouracil, carbamazole), glutathione or a derivative thereof, catechol or a derivative thereof, alcohol or a derivative thereof, zwitterion or a derivative thereof, zwitterionic oligomers, zwitterionic polymers, glycols or a derivative thereof, oligo(ethylene oxide) or a derivative thereof, poly(ethylene oxide) or a derivative thereof, oligo(ethylene imine) or a derivative thereof, poly(ethylene imine) or a derivative thereof, lactic acid or a derivative thereof, oligo(lactic acid) or a derivative thereof, poly(lactic acid) or a derivative thereof, glycolic acid or a derivative thereof, oligo(glycolic acid) or a derivative thereof, poly(glycolic acid) or a derivative thereof, polycaprolactone, amino acid or a derivative thereof, peptide or a derivative thereof, or a protein or a derivative thereof. In some aspects, R comprises an alkyne group, an azide group, a nitrile group, a nitrene group, an amine group, a carbene group, a carbyne group, a urea group, a thioether group, a disulfide group, or a selenolate group. The R group can include amines such as dodecylamine, octadecylamine, or hexylamine.

In some embodiments, the metal entity comprises gold and a —Se-phenyl group as the R group. Non-limiting examples include the $Au_{18}(SePh_{14})$, $Au_{24}(SePh)_{20}$, $Au_{25}((SePh)_{18}$, $Au_{38}(SePh)_{24}$, and $Au_{60}Se_2(PPh)_{10}(SPh)_{15}SBF_6$.

In some embodiments, the metal entity comprises gold and an alkyne as the R group. Non-limiting examples include $Au_8[(C{\equiv}CPh)_2(1,3\text{-dppp})_4]^{2+}$, $Au_{19}(C{\equiv}CPh)_9$(N,N-bis(diphenylphosphinoamine)$_3(SbF_6)_3$, $[Au_{23}(C{\equiv}CPh)_9(PPh_3)_6](SbF_6)_2$, and $[Au_{24}(C{\equiv}CPh)_{14}(PPh_3)_4](SbF_6)_2$.

In some embodiments, the R group comprises a carbene. Non-limiting examples of carbene R groups and exemplary metal entities comprising gold and carbene are shown below.

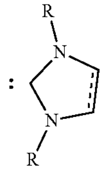

as in

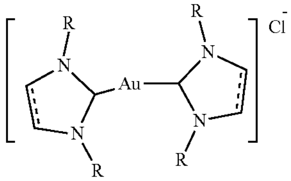

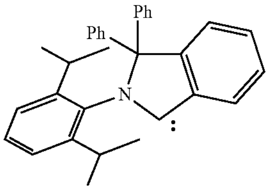

as in

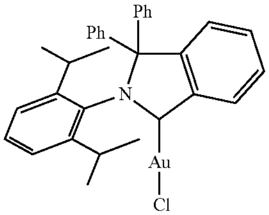

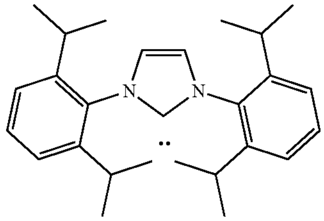

R = $CH_2C_6H_4OCH_3$-p
$CH_2C_6H_4N(CH_3)$-p
$CH_2C_6H_4(CH_3)_3$-2,4,6
$C_2H_5$
$C_5H_9$

The W group in the formula $M_m(R)_r(W)_w(X)_x(Y)_y(Z)_z$ is a thiol or a derivative thereof. W can be derived from unsubstituted or substituted: hydrocarbyl thiol, heterohydrocarbyl thiol, hydrocarbyl disulfide, heterohydrocarbyl disulfide, hydrocarbyl sulfide, heterohydrocarbyl sulfide, hydrocarbyl xanthate, heterohydrocarbyl xanthate, hydrocarbyl thiocarbamate, heterohydrocarbyl thiocarbamate, hydrocarbyl thiourea, heterohydrocarbyl thiourea, hydrocarbyl thiocarbonate, heterohydrocarbyl thiocarbonate, hydrocarbyl thiocarbohydrazide, heterohydrocarbyl thiocarbohydrazide, hydrocarbyl thioamide, heterohydrocarbyl thioamide, hydrocarbyl thiosulfate, heterohydrocarbyl thiosulfate, hydrocarbyl sulfite, heterohydrocarbyl sulfite, hydrocarbyl cyanide, heterohydrocarbyl cyanide, hydrocarbyl glycine, heterohydrocarbyl glycine, hydrocarbyl thiocyanate, heterohydrocarbyl thiocyanate, or a combination thereof.

The W group can include the following structures.

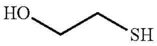
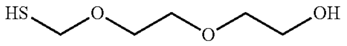
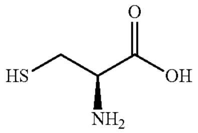
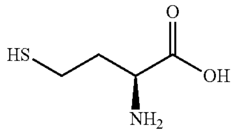
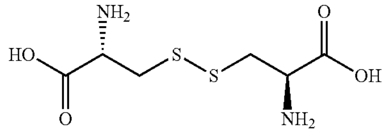
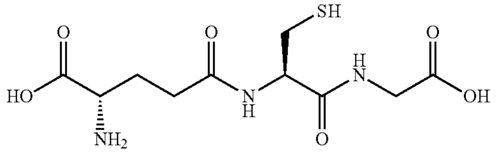
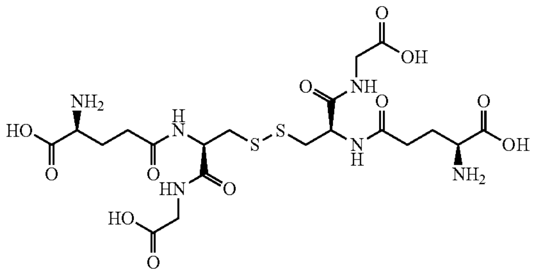
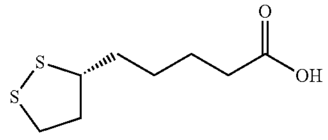
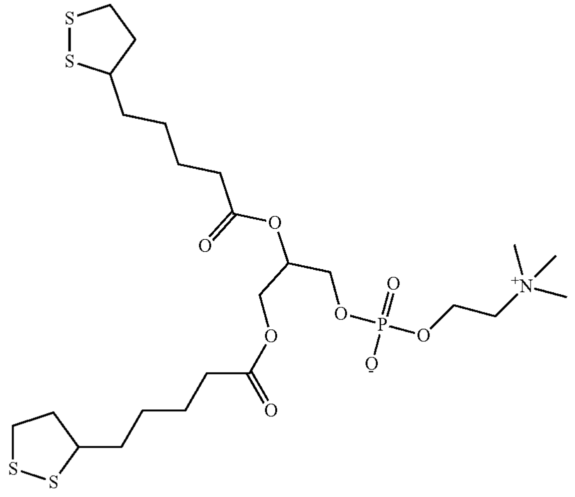
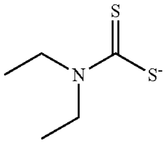
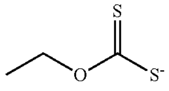

-continued

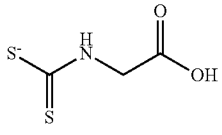
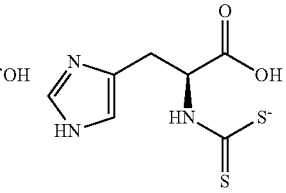
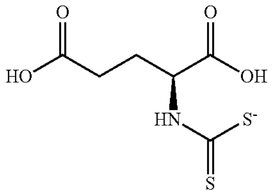

The X group of formula $M_m(R)_r(W)_w(X)_x(Y)_y(Z)_z$ is a phosphine or a derivative thereof. The X group can include unsubstituted or substituted aliphatic groups, unsubstituted or substituted aryl groups, unsubstituted or substituted heteroaryl groups, or a combination thereof.

Exemplary phosphines (X) of formula $M_m(R)_r(W)_w(X)_x(Y)_y(Z)_z$ can include one of compounds 17-1 to 17-12

17-1

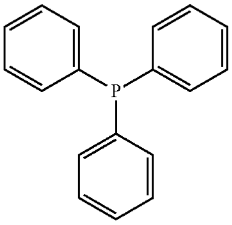

17-2

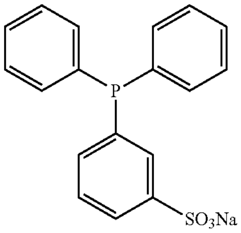

17-3

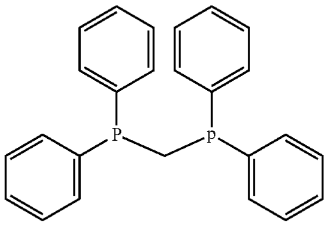

17-4

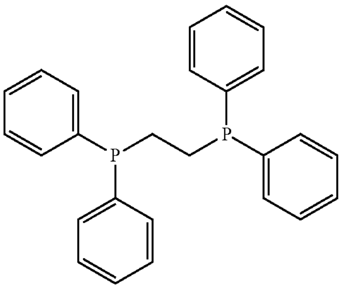

-continued 17-5

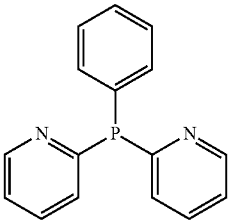

17-6

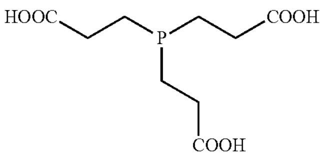

17-7

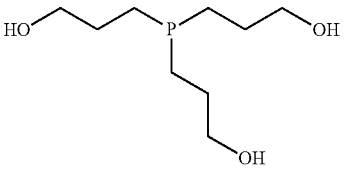

17-8

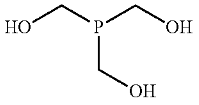

17-9

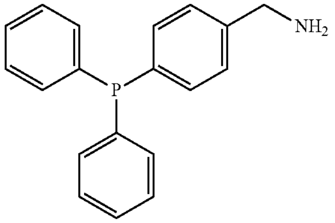

17-10

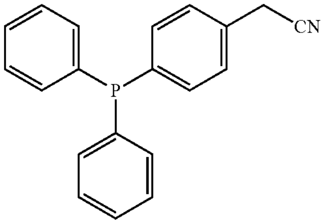

17-11

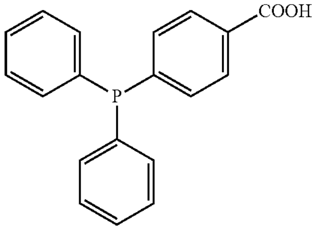

-continued 17-12

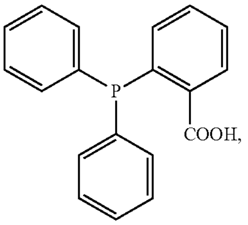
, or a combination thereof.

The Y group of $M_m(R)_r(W)_w(X)_x(Y)_y(Z)_z$ is a carbohydrate or a derivative thereof. The Y group can be derived from is derived from glyceraldehyde, glycerone, threose, erythrose, erythrulose, ribose, arabinose, xylose, lyxose, ribulose, xylulose, allose, altrose, glucose, mannose, galactose, gulose, idose, talose, psicose, fructose, sorbose, tagatose, neuraminic acid, sialic acid, fucose, maltose, sucrose, cellobiose, or trehalose. Exemplary Y groups can be derived from at least one of the following carbohydrate thiols.

18-1

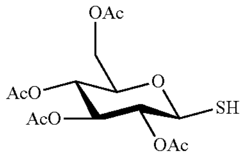

18-2

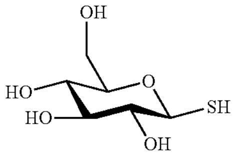

18-3

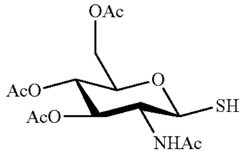

18-4

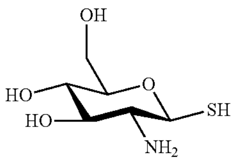

18-5

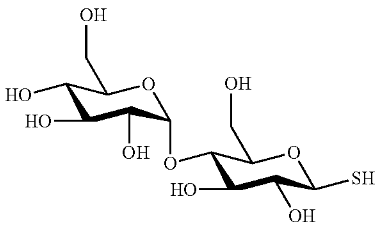

-continued 18-6

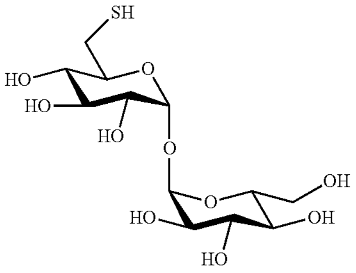

18-7

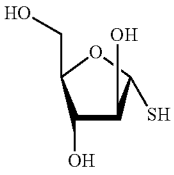

18-8

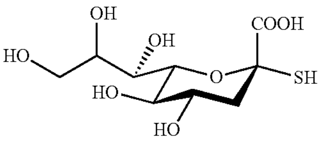

18-9

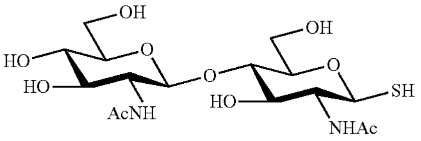

In some aspects, the carbohydrate (Y) of $Au_a(W)_w(X)_x(Y)_y(Z)_z(R)_r$ is derived from $Ac_4Glc$, Glc, $Ac_4GlcN$, GlcN, Mal, or Tre, wherein any hydroxyl of $Ac_4Glc$, $Ac_4GlcN$, Glc, GlcN, Mal, or Tre is replaced with a thiol group to enable coordination to a metal such as gold. In some aspects, the Cl-hydroxyl is replaced with a thiol group. Exemplary carbohydrates (Y) can comprise the following structures, wherein the * indicates attachment to gold.

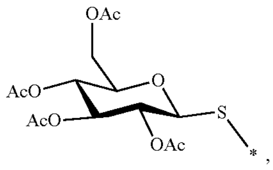

($Ac_4Glc$)

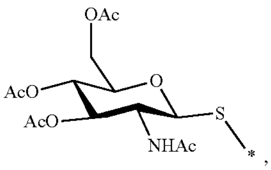

($Ac_4GlcN$)

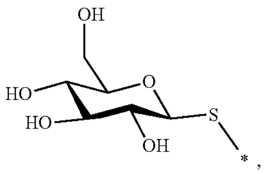

(Glc)

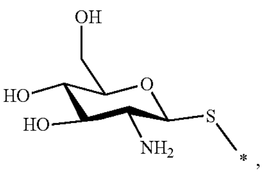

(GlcN)

-continued

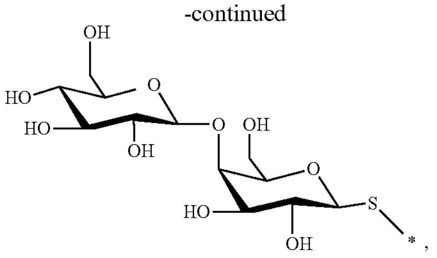

or (Mal)

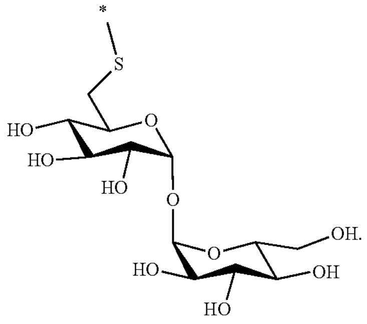

(Tre)

The anion (Z) can be any anion known in the art. The Z groups can include a halide, a sulfonate, a nitrate, a citrate, a cyanide, a perchlorate, a borate, a phosphate, or derivatives thereof.

The disclosed compositions can be used in methods for treating infections including infections caused by bacteria, biofilm, parasites, fungi, viruses, protozoa, and/or worms.

The methods comprise administering a therapeutically effective amount of a composition comprising a metal entity and an activating agent to treat a bacterial infection. The bacterial infection can be caused by a gram-negative bacterium, a gram-positive bacterium, an ESKAPE pathogen, *Escherichia* sp., mycobacteria, *Pseudomonas* sp., *Burkholderia* sp., *Helicobacter* sp., *Borrelia* sp., or a combination thereof. In some embodiments, the bacterial infection is caused by gram-negative bacteria. In some embodiments, the bacterial infection is caused by gram-positive bacteria. In some embodiments, the bacterial infection is caused by an ESKAPE pathogen. In some embodiments, the bacterial infection is caused by *Escherichia* sp. In some embodiments, the bacterial infection is caused by mycobacteria. In some embodiments, the bacterial infection is caused by *Pseudomonas* sp. In some embodiments, the bacterial infection is caused by *Burkholderia* sp. In some embodiments, the bacterial infection is caused by *Helicobacter* sp. In some embodiments, the bacterial infection is caused by *Borrelia* sp.

The disclosed methods for treating a bacterial infection can further include administering an effective amount of an antibacterial agent in combination with the composition including the metal entity and the activating agent. As used herein, an "antibacterial agent" can destroy or inhibit the growth of bacteria and are familiar to one of skill in the art. Antibacterial agents suitable for pharmaceutical use include a variety of agents, e.g., from groups such as penicillins, cephalosporins, glycopeptide derivatives, carbapenems, aminoglycosides, macrolides, tetracyclines, chloramphenicol, ansamycins, lincomycins, sulfonamides, metronidazole, nitroimidazoles, phenicols, pyrimidine derivatives, rifampin, or quinolones. In a particular embodiment, antibacterial agents for use in the methods and compositions of the instant invention include, e.g., colistin, amikacin, gentamicin, tobramycin, meropenem, imipenem, cefazolin, cefepime, cefoxitin, cephalothin, ceftazidime, cefotaxime, cefoperazone, ceftriaxone, cefuroxime, levofloxacin, ciprofloxacin, nitrofurantoin, trimethoprim/sulfamethoxazole, linezolid, vancomycin, erythromycin, clindamycin, daptomycin, mupirocin, ampicillin, piperacillin, oxacillin, penicillin, mezlocillin, amoxicillin, aztreonam, sulfisoxazole, chloramphenicol, streptomycin, tetracycline, minocycline, rifampin, or silver sulfadiazine.

The methods comprise administering a therapeutically effective amount of a composition including the metal entity and the activating agent to treat a biofilm infection. The methods can further comprise administering a therapeutically effective amount of an anti-biofilm agent in combination with the composition including the metal entity and the activating agent. As used herein, "anti-biofilm agents" can destroy or inhibit the growth of a biofilm and are familiar to one of skill in the art. In some aspects, the biofilm is a *Pseudomonas aeruginosa* infection. Such infections can include chronic wounds, chronic otitis media, chronic prostatitis and chronic lung infections (e.g., cystic fibrosis).

The methods comprise administering a therapeutically effective amount of a composition including the metal entity and the activating agent to treat a parasitic infection. The methods can further comprise administering a therapeutically effective amount of an anti-parasitic agent in combination with the metal entity and the activating agent. As understood herein, "antiparasitic agents" can kill, inhibit and/or otherwise control parasite growth. Non-limiting exemplary antiparasitic agents include amitraz, aminoacetonitriles, albendazole, cambendazole, fenbendazole, flubendazole, thiabendazole, mebendazole, cyclic octadepsipeptides, oxfendazole, oxibendazole, paraherquamide, parbendazole, piperazines, praziquantel, tetramisole, triclabendazole, levamisole, pyrantel (including the salt forms such as pamoate, citrate, and tartrate), oxantel, morantel, abamectin, doramectin, emamectin, eprinomectin, ivermectin, moxidectin, selamectin, dimadectin, latidectin, lepimectin, milbemycin, milbemycin oxime, demiditraz, emodepside, fipronil, methoprene, diethylcarbamazine, hydroprene, kinoprene, lufenuron, metaflumizone, niclosamide, permethrin, pyrethrins, pyriproxyfen, closantel, clorsulon, novaluron, fluazuron, spinosad, sarolaner, fluralaner, afoxolaner, lotilaner, or a combination thereof.

The methods comprise administering a therapeutically effective amount of a composition including the metal entity and the activating agent to treat a fungal infection. In some embodiments, the fungal infection includes a yeast infection. In some embodiments, the fungal infection includes a *Candida* infection, an *Aspergillus* infection, a *Cryptococcus* infection, or a combination thereof. The methods can further comprise administering a therapeutically effective amount of an anti-fungal agent in combination with the composition including the metal entity and the activating agent. As understood herein, "antifungal agents" can kill, inhibit and/or otherwise control fungal growth. Exemplary antifungal agents include azoles, echinocandins, nucleoside analogs and polyenes. Such compounds include tolnaftate, amorolfine, ciclopirox olamine, flucytosine, griseofulvin, haloprogin, potassium iodide, sodium pyrithione, undecylenic acid, bifonazole, butoconazole, clotrimazole, isoconazole, tioconazole, econazole, ketoconazole, miconazole, oxiconazole, sertaconazole, sulconazole, itraconazole, fluconazole, terconazole, voriconazole, naftifine, butenafine, and terbinafine. Antifungal antibiotics include amphotericin B, caspofungin, anidulafungin, micafungin and nystatin.

The methods comprise administering a therapeutically effective amount of a composition comprising the metal entity and the activating agent to treat a worm infection. The methods can further comprise administering a therapeutically effective amount of an anti-worm agent in combination with the composition including the metal entity and the activating agent. As understood herein, "anti-worm agents" can kill, inhibit and/or otherwise control worm growth. Exemplary anti-worm agents include a benzimidazole, such as albendazole, mebendazole, thiabendazole, and the like; and abamectin; diethylcarbamazine; pyrantel pamoate; levamisole; salicylanilide; nitrazoanide; and praziquantel.

The methods comprise administering a therapeutically effective amount of a composition comprising the metal entity and the activating agent to treat a protozoan infection. The protozoan infection can include a protozoal parasite infection, a pathogenic trichomonad infection, or a combination thereof. The methods can further comprise administering a therapeutically effective amount of an anti-protozoal agent in combination with the compositions comprising the metal entity and the activating agent. As understood herein, "anti-protozoal agents" can kill, inhibit and/or otherwise control protozoal growth. Exemplary anti-protozoal agents include eflornithine, furazolidone, hydroxychloroquine, melarsoprol, metronidazole, nifursemizone, ornidazole, paromomycin sulfate, pentamidine, pyrimethamine, quinapyramine, and tinidazole.

The methods comprise administering a therapeutically effective amount of a composition comprising the metal entity and the activating agent to treat a viral infection. The methods can further comprise administering a therapeutically effective amount of an anti-viral agent in combination with the compositions comprising the metal entity and the activating agent. As understood herein, "anti-viral agents" can kill, inhibit and/or otherwise control viral replication. The viral infection virus can include coronavirus infection, for example, a SARS-CoV-2 infection, a SARS-CoV-1 infection, a MERS-CoV infection, or a combination thereof. The viral infection can include an HIV infection, a hepatitis C infection, a Zika infection, a chikungunya infection, a vaccinia infection, a dengue viral infection, or a combination thereof.

The disclosure includes methods of inhibiting the growth of a bacterium in vitro or in vivo comprising contacting a bacterium with an effective amount of a metal entity or salt and an activating agent according to any one of the foregoing. The bacterium can be caused by a gram-negative bacterium, a gram-positive bacterium, a *mycobacterium*, an ESKAPE pathogen, *Escherichia* sp., *Pseudomonas* sp., *Helicobacter* sp., *Burkholderia* sp., *Borrelia* sp., or a combination thereof. In some embodiments, the bacterium is a gram-negative bacterium. In some embodiments, the bacterium is a gram-positive bacterium. In some embodiments, the bacterium is an ESKAPE pathogen. In some embodiments, the bacterium is *Escherichia* sp. In some embodiments, the bacterium is a *mycobacterium*. In some embodiments, the bacterium is a *Pseudomonas* sp. In some embodiments, the bacterium is *Burkholderia* sp. In some embodiments, the bacterium is *Helicobacter* sp. In some embodiments, the bacterium is *Borrelia* sp.

Methods for inhibiting the growth of a biofilm in vitro or in vivo comprise contacting a biofilm with an effective amount of a metal entity or salt and an activating agent according to any one of the foregoing. The methods for inhibiting the growth of a biofilm in vitro or in vivo can further comprise administering an effective amount of an anti-biofilm agent.

Methods for inhibiting the growth of a parasite in vitro or in vivo comprise contacting a parasite with an effective amount of a metal entity or salt and an activating agent according to any one of the foregoing. The methods for inhibiting the growth of a parasite in vitro or in vivo can further comprise administering an effective amount of an anti-parasite agent. The parasites can include *Toxoplasma gondii* parasite that causes toxoplasmosis and *Trypanosoma cruzi* that causes Chagas disease.

Methods for inhibiting the growth of a fungus in vitro or in vivo comprise contacting a fungus with an effective amount of a metal entity or salt and an activating agent according to any one of the foregoing. In some embodiments, the fungus is a yeast. In some embodiments, the fungus is *Candida, Aspergillus, Cryptococcus*, or a combination thereof. The methods for inhibiting the growth of a fungus in vitro or in vivo can further comprise administering an effective amount of an anti-fungal agent.

Methods for inhibiting the replication of a virus in vitro or in vivo comprise contacting a virus with an effective amount of a metal entity or salt and an activating agent according to any one of the foregoing. The methods for inhibiting the replication of a virus in vitro or in vivo can further comprise administering an effective amount of an anti-viral agent. The virus can include coronaviruses, for example SARS-CoV-2, the virus that causes COVID-19; SARS-CoV-1, the virus that causes SARS; MERS-CoV, the virus that causes MERS. The virus can include human immunodeficiency virus (HIV), hepatitis C virus (HCV), Zika virus, chikungunya virus, vaccinia virus, dengue virus or a combination thereof.

Methods for inhibiting the growth of a protozoan in vitro or in vivo comprise contacting a protozoan with an effective amount of a metal entity or salt and an activating agent according to any one of the foregoing. The methods for inhibiting the growth of a protozoan in vitro or in vivo can further comprise administering an effective amount of an anti-protozoal agent. The protozoans can include trichomonads, for example, *Trichomonas vaginalis* that causes trichomoniasis, *Dientamoeba fragilis, Histomonas meleagridis*, and *Mixotricha paradoxa*. The protozoans can include protozoal parasites, for example, *Cryptosporidium, Giardia*, and *Entamoeba histolytica*.

Methods for inhibiting the growth of a worm in vitro or in vivo comprise contacting a worm with an effective amount of a metal entity or salt and an activating agent according to any one of the foregoing. The methods for inhibiting the growth of a worm in vitro or in vivo can further comprise administering an effective amount of an anti-worm agent. The protozoans can include tapeworm *Taenia solium* that causes neurocysticercosis, and roundworms that causes toxocariasis.

In any of the foregoing methods, the metal entity or salt and the activating agent can be added in any order. In some embodiments, the metal entity or salt is added at the same time with the activating agent. In some embodiments, the metal entity is added prior to the addition of the activating agent. In some embodiments, the metal entity is added after the addition of the activating agent.

The compositions can be administered as the neat composition or administered as a pharmaceutical composition. Accordingly, an embodiment provides pharmaceutical compositions comprising a metal entity and an activating agent or pharmaceutically acceptable salts thereof, together with a pharmaceutically acceptable carrier. The pharmaceutical composition may contain a metal entity and an activating agent as the only active agent, or may contain one or more additional active agents or a carrier.

The compositions may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients, diluents, or drug delivery vehicles, and must be of sufficiently high purity and sufficiently low toxicity to render them suitable for administration to the patient being treated. The carrier can be inert or it can possess pharmaceutical benefits of its own. The amount of carrier employed in conjunction with the composition is sufficient to provide a practical quantity of material for administration per unit dose of the compound.

Classes of carriers include, for example, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Exemplary pharmaceutically acceptable carriers also include chitosan, chitin, liposomes and polymer micelles made from copolymers of hydrophilic-hydrophobic blocks. The hydrophilic block includes poly(ethylene glycol) (PEG), poly(ethylene oxide) (PEO), poly(N-vinyl pyrrolidone) (PVP) and poly(N-isopropyl acrylamide) (pNIPAM). The hydrophilic block includes include poly(lactic acid) (PLA), poly(glycolic acid) (PGA), polycaprolactone (PLC), polyamides such as poly (L-lysine) (PLL), and poly (beta-amino ester). Optional active agents may be included in a pharmaceutical composition, which do not substantially interfere with the activity of the disclosed compositions.

The pharmaceutical compositions can be formulated for oral administration. These compositions contain between 0.1 and 99 weight percent ("wt. %") of the disclosed compositions and usually at least about 5 wt. %. Some embodiments contain from about 25 wt. % to about 50 wt. % or from about 5 wt. % to about 75 wt. % of the disclosed compositions.

The pharmaceutical compositions can be formulated in a package comprising the pharmaceutical composition of the disclosed compositions in a container and further comprising instructions for using the composition in order to elicit a therapeutic effect in a patient.

EXAMPLES

Example 1: Synthetic Procedures

Scheme 1.

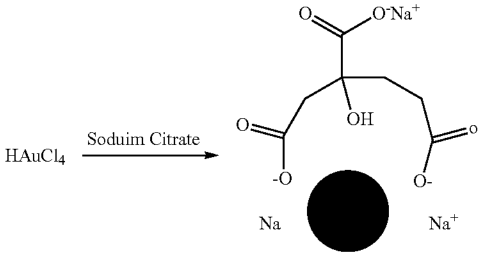

Synthesis of citrate-protected 13 nm gold nanoparticles. $HAuCl_4$ was dissolved in water (100 mL, 1% w/v) and heated to boiling for 10 min. Sodium citrate dihydrate (4 mL, 1% w/v) was added rapidly and the reaction mixture was stirred for an additional 30 min. The solution was cooled to room temperature and then washed with water followed by centrifugation at 5,000 rcf for 5 min (twice) to remove unreacted small molecules. The red precipitate was collected and stored in 4 mL of water.

Scheme 2.

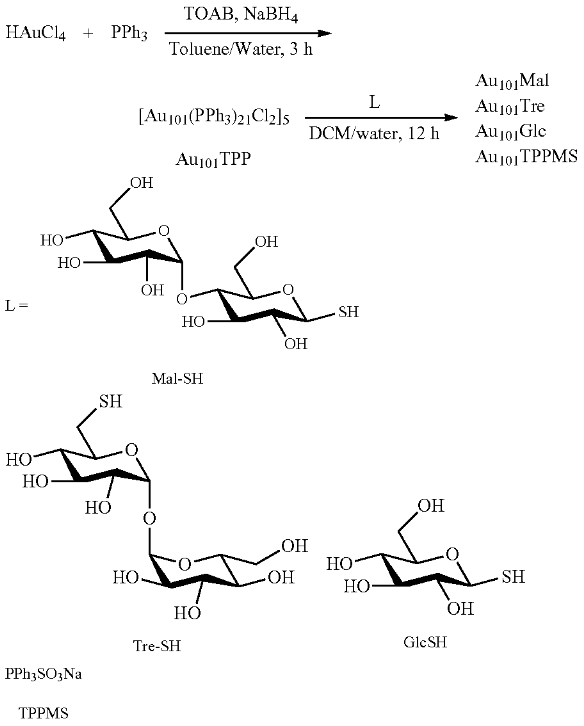

Synthesis of $Au_{101}$TPP. A biphasic mixture of toluene/water (19.5 mL/15 mL) was purged with argon for 1 h. To this, tetraoctylammonium bromide, TOAB (0.89 mmol) and tetrachloroauric(III) acid trihydrate, $HAuCl_4 \cdot 3H_2O$ (0.76 mmol) were added, and the reaction mixture was stirred for 10 min. After this, triphenylphosphine (2.66 mmol) was added and the resulting mixture stirred for a further 10 min until the organic phase was white and cloudy. $NaBH_4$ (11 mmol) was dissolved in water (3 mL) and immediately added to the reaction flask. Argon was continuously bubbled into the flask for 2 h, then the flask was capped and the mixture stirred for 1 more hour. The reaction mixture was then washed with water (50 mL×3) and the organic layer was isolated. The crude product was dispersed in hexanes by sonication and then filtered through a medium porosity frit. The clusters were then washed successively with the following solvent systems; each step was repeated 3 times: 1) hexanes (30 mL) followed by MeOH:water/2:3 (v/v, 30 mL), 2) hexanes (30 mL) followed by a saturated aqueous solution of $NaNO_2$ (30 mL), and 3) hexanes (30 mL) followed by MeOH:water/2:3 (v/v, 30 mL). The clusters were then dissolved in $CHCl_3$ (5 mL) and precipitated using pentane at a slow addition rate of 5 mL/h. This precipitation process was repeated 3 times, and, after filtration, $Au_{101}$ was obtained as a black solid (43 mg).

Synthesis of $Au_{101}$Mal ($Au_{101}$Tre, $Au_{101}$Glc and $Au_{101}$TPPMS were prepared similarly using the corresponding ligands). $Au_{101}$TPP (0.474 μmol) was dissolved in dichloromethane (DCM, 3 mL). D-Maltose-SH (47.4 μmol) was dissolved in water (3 mL) and added to the reaction flask. The reaction mixture was stirred at room temperature overnight (12 h). The aqueous layer was then washed with DCM (3×5 mL) to remove organic exchange byproducts, after which the aqueous solution was lyophilized. The product was then dissolved/dispersed in water (7 mL) and the resulting mixture suspended in a dialysis tube (MWCO 3.0-5.0 kDa.) while stirring in water (500 mL) for 24 h. The water was refreshed every 4 h. After lyophilization, the product was obtained as a black solid (8 mg).

Scheme 3.

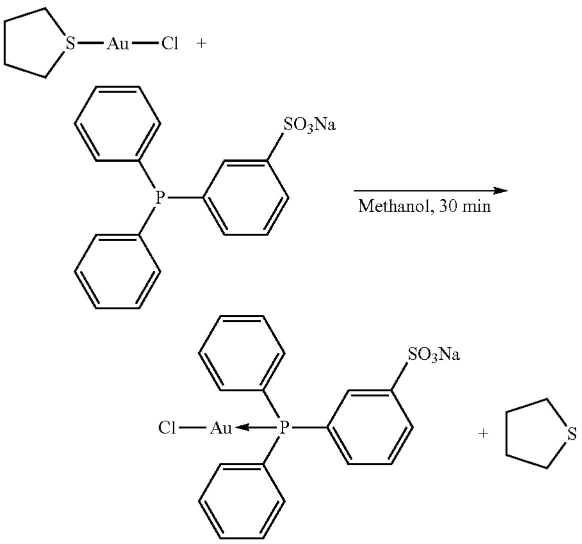

[AuTPPMS]Cl

Synthesis of [AuTPPMS]Cl. To a stirred solution of chloro(tetrahydrothiophene) gold(I) (0.2 g, 0.62 mmol) in methanol (35 mL), triphenylphosphine-3-sulfonate (0.23 g, 0.62 mmol) was added. The solution was stirred for 40 min and then filtered through a bed of Celite® and then precipitated from methanol twice with $Et_2O$.

Synthesis of $Au_{18}SG_{14}$. $HAuCl_4 \cdot 3H_2O$ (0.15 g, 0.38 mmol) was dissolved in methanol (1.2 mL), then glutathione (GSH, 0.30 g, 0.98 mmol) was added forming a colorless solution. The mixture was stirred for 5 minutes then diluted to 30 mL by methanol. To this mixture, $NaBH_3CN$ (63 mg, 10 mmol) was added and the reaction was stirred for 5 h after which a precipitate forms. The precipitate was purified by washing with methanol to obtain $Au_{18}SG_{14}$.

Synthesis of $Au_{22}SG_{18}$. An aqueous solution of $HAuCl_4 \cdot 3H_2O$ (94 mg, 0.24 mmol) in water (19 mL) was combined with glutathione (0.12 g, 0.38 mmol) diluted in water (15 mL). The reaction was diluted to 220 mL and stirred for 2 min to form a cloudy yellow solution. The pH was then adjusted to 12.0 using 1 M NaOH then $NaBH_4$ (1.6 mg, 4.2 μmol) in water (1.2 mL) was added dropwise and the solution was left to stir for 30 min. The pH of the solution as then lowered to 2.5 using 5 M HCl, and the reaction stirring speed was lowered to 150 rpm and continued for 6 h. $Au_{22}SG_{18}$ was then precipitated by addition of isopropyl alcohol. Synthesis of $Au_{25}SG_{18}$. $HAuCl_4 \cdot 3H_2O$ (20 mg, 5 μmol) in water (0.4 mL) was combined with glutathione (4.6 mg, 15 μmol) in water (1.5 mL) and diluted to 6 mL. The pH of the solution was adjusted to 2.0 by addition of 1 M $HNO_3$. The mixture was then stirred for 5 minutes followed by rapid addition of t-butylamine borane (TBAB, 4.3 mg, 50 μmol) in toluene (5 mL). The reaction was stirred for 6 h then excess methanol was added to precipitate $Au_{25}SG_{18}$.

Example 2: Evaluation of Antibacterial Activities and Cytotoxicity to Mammalian Cells Antibacterial assay. All bacteria were cultured and assayed in cation-adjusted Mueller Hinton broth (CAMHB). A freshly inoculated culture was incubated overnight (12 h) at 37° C. The obtained culture was then used to prepare a 0.5 McFarland standard-matched culture (≈$1.5\times10^8$ CFU/mL) using a Tecan Infinite® Pro multiplate reader. The culture was then diluted to a final density of $1\times10^6$ CFU/mL. Volumes (100 μL) of this culture solution were combined, in 96-well plates, with equal volumes of gold entities serially diluted in broth for a final bacteria concentration of $5\times10^5$ CFU/mL. In order to confirm the CFU density, a spread plate from the final inoculum was also prepared to contain a count of between 30-300. All the plates were covered and incubated at 37° C. for 18 h without shaking. The inhibition of bacterial growth was determined measuring the absorbance at 600 nm ($OD_{600}$).

Bacterial Checkerboard Assay. A freshly inoculated culture was incubated overnight (12 h) at 37° C. The obtained culture was then used to prepare a 0.5 McFarland standard-matched culture (~$1.5\times10^8$ CFU/mL) and then diluted 150-fold with CAMHB. Aliquots (100 μL) of this culture solution was added to the antibiotic dilution panels, in 96-well plates, for a final bacteria concentration of $5\times10^5$ CFU/mL. In order to confirm the CFU density, a spread plate from the final inoculum was also prepared to contain a count of between 30-300. The antibiotic panels were prepared by 2-D dilutions. First, gold entities were prepared as a stock solution (4.1 mg/mL) and serially diluted horizontally in a 96-well plate. Next, thiourea was serially diluted vertically. The bacteria culture solution prepared was then added and the plate was incubated at 37° C. for 18 h. The MICs were read visually and spectrophotometrically with and without alamarBlue® reagent.

The fractional inhibitory concentration (FIC) index values of the combined thiourea and gold entities were calculated by the formula $$FIC = \frac{A}{MIC\ A} + \frac{B}{MIC\ B}$$

wherein A is the concentration of A (gold entity) in a row and B is the concentration of B (thiourea) in the same well, and MIC A and MIC B are independent MICs of the two compounds. The FIC is a measure of the synergy between co-administered compounds, with values <0.5 considered synergetic, 0.5-4 as additive or indifferent, and >4 as antagonistic.

Cytotoxicity Assay. A549 human lung carcinoma epithelial cells (ATCC® CCL-185™) and NIH/3T3 mouse fibroblast cells (ATCC® CRL-1658™) were cultured in Dulbecco's modified Eagle medium (DMEM) supplemented with L-glutamine (4 mM), sodium pyruvate (1 mM) fetal bovine serum (10%), and 1% of antibiotics (penicillin/streptomycin, gentamicin sulfate and amphotericin B). Cells were obtained from culture, counted using a Countess™ automated cell counter, and then seeded at 4,000 cells per well in 96-well plates and left to attach for 12 h in a 37° C./5% $CO_2$ air-humidified incubator.

Samples were prepared in working concentrations in complete media from a stock solution (4.1 mg/mL). Gold entities were serially diluted horizontally in volumes of media (100 μL), followed by serial dilution of thiourea vertically into the same wells to create a checkerboard of both compounds. These plates were then incubated for 30 min at 37° C. to bring the media to optimum cell temperature.

After the cellular-attachment incubation time, the media was removed carefully. Volumes of of the previously prepared gold entity/thiourea solutions (80 μL) were added to the cells in all 96 wells. The cells were then incubated for 18 h in a 37° C./5% $CO_2$ air-humidified incubator. After 18 h, the cells were washed with DPBS (without $Ca^{2+}$ or $Mg^{2+}$) twice, after which volumes of 10% alamarBlue® cell viability reagent (80 μL) containing complete cell media was added to the wells and plates were incubated for 2.5 h in a 37° C./5% $CO_2$ air-humidified incubator. After incubation, fluorescence values were obtained with excitation/emission wavelengths of 560/590 nm. The viability was expressed relative to an untreated control.

Biofilm assay using Innovotech MBEC Assay® plates. The turbidity of overnight grown bacterial cultures was adjusted to 0.5 McFarland standard and then the bacterial suspension was diluted to $1\times10^5$ CFU/mL in CAMHB. Volumes of 150 μL aliquots were transferred into Innovotech MBEC Assay® plates. The biofilms were established in these biofilm inoculators by incubating bacterial suspensions at 37° C. for 24 h with rotation at 150 rpm. In a separate antimicrobial challenge plate, $Au_{101}$Mal was serially diluted in 7 mM TU in 200 μL volume. The biofilms pegs were washed with 0.85% saline (200 μL) then immersed in the challenge plate and incubated at 37° C. for 6 h at 150 rpm. The pegs were then rinsed with a 100 μg/mL reduced glutathione solution (200 μL) to neutralize the antimicrobials, and equilibrated again in the same solution (200 μL) for 20 min followed by a sonication time of 30 min to dislodge the biofilms into 200 μL of 0.85% saline. These dislodged biofilms were then serially diluted in 0.85% saline and plated on LB agar to count the colonies.

Biofilm assay using crystal violet staining. The turbidity of overnight grown bacterial cultures was adjusted to 0.5 McFarland standard and then the bacterial suspension was diluted to $1\times10^5$ CFU/mL in CAMHB. Volumes of 100 μL aliquots were transferred into 96 well plates. The plates were incubated at 37° C. for 24 h with rotation at 150 rpm to establish the biofilms. After the incubation, the culture was carefully removed, and wells were washed with 0.85% saline (0.13 mL×3). In a separate plate, $Au_{101}$Mal was serially diluted in CAMHB, and volumes of 75 μL of these were transferred to biofilm-containing wells while maintaining the serial-dilution trend. Aliquots of 75 μL of TU-supplemented (14 mM) CAMHB were also transferred to these wells, except the growth control and blank, to maintain a 150 μL of challenge volume. The plates were then incubated at 37° C. for 6 h at a rotation of 150 rpm. The challenged cultures were removed by tilting the plates and carefully pipetting the contents out. The wells were washed with 0.85% saline (180 μL×3). Any remaining saline was carefully pipetted out and then plates were dried for 5 min. Then, volumes of 180 μL of 0.1% crystal violet (CV) solution was added to each well, and the plates were left to stain for 15 min at room temperature. After staining, CV was removed by pipetting and the wells were washed with 0.85% saline (210 L×3). Any remaining saline was carefully pipetted out and then plates were dried for 10 min. After adding volumes of 220 μl of 30% acetic acid to solubilize CV, the plates were incubated for 30 min at room temperature. While maintaining the order, volumes of 150 μL of these solutions were transferred to a new 96 well plate, and the absorbance at 595 nm was measured.

Activation of intracellular Au. An overnight culture of *P. aeruginosa* PAO1 was allowed to grow to $OD_{600}$ of 0.4. 1 mL of this solution was pelleted (3,000 g for 5 minutes) then washed with PBS (3×1 mL) then pelleted. $Au_{101}$Mal (1 mg/mL in 1 mL PBS) was added to this solution and the mixture shaken at 180 rpm at 37° C. for 15 min to allow uptake. Bacteria were then pelleted and non-internalized AuNC was washed away with PBS (3×1 mL). PAO1 with internalized $A_{101}$Mal was resuspended in 1 mL PBS and added in 100 μL volumes to a serial dilution of TU in CAMHB.

To investigate the ability of thiourea to affect the activity of the gold entities, thiourea (TU) was co-administered using a checkerboard assay on *Pseudomonas aeruginosa* PAO1. Table 1 shows the fractional inhibitory concentration (FIC) indices obtained from a 96-well plate of TU co-administered with $Au_{101}$Mal. The bold values are the concentrations of Au in $Au_{101}$Mal (horizontal) and TU (vertical), respectively. The bolded numbers represent no bacteria growth, and the other regions represent bacteria growth.

TABLE 1

| | $Au_{101}$Mal | | | | | | | | | | | |
|---|---|---|---|---|---|---|---|---|---|---|---|---|
| TU | 344 μM | 172 μM | 86 μM | 43 μM | 22 μM | 11 μM | 5.4 μM | 2.7 μM | 1.3 μM | 0.67 μM | 0.34 μM | 0 μM |
| 108 mM | **1.00** | **0.75** | **0.63** | **0.56** | **0.53** | **0.52** | **0.51** | **0.50** | **0.50** | **0.50** | 0.50 | |
| 54 mM | **0.75** | **0.50** | **0.38** | **0.31** | **0.28** | **0.27** | **0.26** | **0.25** | **0.25** | **0.25** | 0.25 | |
| 27 mM | **0.63** | **0.38** | **0.25** | **0.19** | **0.16** | **0.14** | **0.13** | **0.13** | **0.13** | **0.13** | 0.13 | |
| 13 mM | **0.56** | **0.31** | **0.19** | **0.13** | **0.09** | **0.08** | **0.07** | **0.07** | **0.06** | 0.06 | 0.06 | |
| 7 mM | **0.53** | **0.28** | **0.16** | **0.09** | **0.06** | **0.05** | **0.04** | **0.04** | **0.03** | 0.03 | 0.03 | |
| 3 mM | **0.52** | **0.27** | **0.14** | **0.08** | **0.05** | **0.03** | **0.02** | **0.02** | 0.02 | 0.02 | 0.02 | |
| 2 mM | **0.51** | **0.26** | **0.13** | **0.07** | **0.04** | **0.02** | **0.02** | 0.01 | 0.01 | 0.01 | 0.01 | |
| 0 mM | | | | | | | | | | | | |

The FIC values were calculated according to equation 1. In the unshaded regions with no growth, the lowest value possible is the best FIC. As $Au_{101}$Mal did not have an MIC up to the highest concentration tested (344 μM), a hypothetical value of 688 μM was used to calculate FIC. TU was independently observed to have an MIC of 16 mg/mL.

Table 2 are the MICs of $Au_{101}$Mal at different concentrations of added TU, extracted from the data in Table 1.

TABLE 2

| | TU added | | | | | | |
|---|---|---|---|---|---|---|---|
| | 0 mM | 2 mM | 3 mM | 7 mM | mM | 27 mM | 54 mM |
| MIC of $Au_{101}$Mal (μM [Au]) | >344 | 5.4 | 2.7 | 1.3 | 1.3 | 0.67 | 0.67 |

$Au_{101}$Mal does not kill the bacteria at concentrations up to 344 μM [Au] (higher concentrations not yet determined). When 2 mM of TU was added, the MIC of $Au_{101}$Mal decreased drastically to 5.4 μM [Au], and further to 0.7 μM [Au] with the addition of 27 mM TU, making it an antimicrobial agent against *Pseudomonas aeruginosa*. As a reference, the MIC of colistin, a last-resort antibiotic, is 1 μg/mL, and that of erythromycin is 256-512 μg/mL against *P. aeruginosa* PAO1.

In the above system, the best FIC value obtained was 0.05 showing strong synergy between both compounds. Note that neither $Au_{101}$Mal nor TU are toxic unless at very high concentrations. The experiment was repeated with other gold entities which all showed a marked increase in antipseudomonal activity (see Table 3). The MIC difference was particularly impressive with gold entities having carbohydrate groups (128-fold enhancement; entries 4 and 5), implying that the carbohydrate ligand may also participate in enhancing the antimicrobial activity, perhaps through different mechanisms like facilitated uptake. TU had no impact on the activities of common antibiotics (entries 8 and 9).

Table 3 shows the MICs of gold entities and antibiotics with and without TU, and the fold improvement in MIC at the best fractional inhibitory concentrations.

TABLE 3

| Entry | Compound | Best FIC | [TU] (mM) | MIC with TU | MIC w/o TU | Fold Improvement in MIC |
|---|---|---|---|---|---|---|
| 1 | [AuTPPMS]Cl | 0.0313 | 3.36 | 1.83 μM | 234 μM | 128 |
| 2 | $[Au_9(TPPMS)_8]Cl_3$ | 0.0234 | 1.68 | 8.83 μM | 283 μM | 32 |
| 3 | $Au_{101}(TPPMS)_{21}Cl_5$ | 0.0332 | 0.42 | 3.25 μM | 104 μM | 32 |
| 4 | $Au_{101}(TPPMS)_{19}(Ac_4Glc)_2Cl_5$ | 0.0234 | 1.68 | 11.85 μM | 237 μM | 128 |
| 5 | $Au_{101}(TPPMS)_{14}(Ac_4Glc)_7Cl_5$ | 0.0469 | 3.36 | 4.06 μM | 520 μM | 128 |
| 6 | $Au_{101}(TPPMS)_{11}(Ac_4Glc)_{10}Cl_5$ | 0.0195 | 0.84 | 1.60 μM | 102 μM | 64 |
| 7 | $Au_{101}(TPPMS)_7(Ac_4Glc)_{14}Cl_5$ | 0.0313 | 3.36 | 1.68 μM | 107 μM | 64 |
| 8 | Gentamicin | 1.0 | 0-108 | 4.0 μM | 4.0 μM | 1 |
| 9 | Piperacillin | 1.0 | 0-108 | 2.0 μM | 2.0 μM | 1 |

Figure 1B:
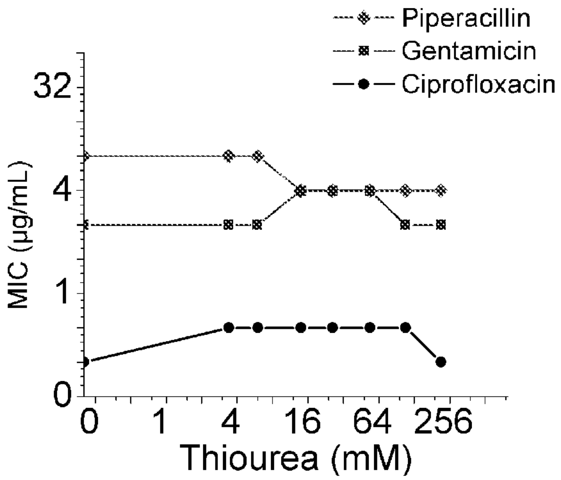

The isobologram in FIG. 1A shows the drastic decrease in MICs against *P. aeruginosa* PAO1 with the combination of thiourea with $Au_{101}$Mal, AuNP-citrate or $Au_{101}$Tre. Piperacillin, gentamicin or ciprofloxacin were assayed together with thiourea, however resulting in very little change in activity (FIG. 1B).

The toxicity of thiourea to humans is low, having been used in hyperthyroidism treatment at dosages up to 3 g/day before it was discontinued.

Figure 2A:
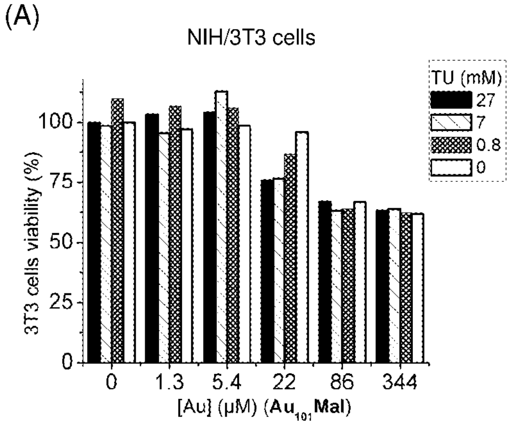
FIGS. 2A-2B show the viability of NIH/3T3 cells (FIG. 2A) and A549 cells (FIG. 2B), treated with a combination of different concentrations of TU and $Au_{101}$Mal, in which the Au concentrations were quantitated by ICP-MS.
Figure 2B:
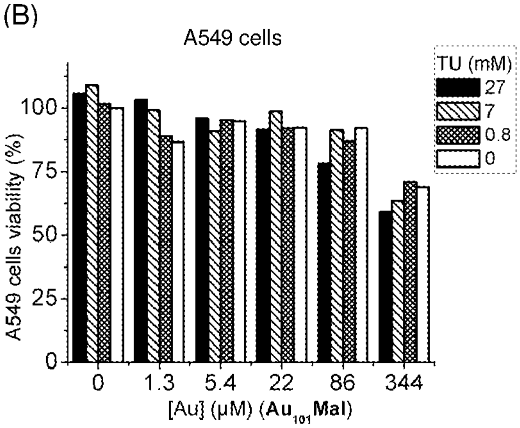

A preliminary cytoxicity study of the combination of $Au_{101}$Mal was tested on adherent cell lines of mouse fibroblast cells (NIH/3T3) and human lung carcinoma epithellial cells (A549). Analogous to the bacterial tests, a checkerboard assay was conducted where TU/AuNC dilutions were prepared in a separate plate prior to addition to attached cells. FIG. 2A shows that the NIH/3T3 cells remained viable at 27 mM/5.4 μM TU/$Au_{101}$Mal. FIG. 2B shows that the A549 cells remained viable at 27 mM/86 μM TU/$Au_{101}$Mal.

Table 4. MICs on *P. aeruginosa* PAO1 (μM) of gold entities (expressed as [Au]) vs. the concentrations of added TU (mM).

TABLE 4

| Gold entity | MIC (0 mM TU) | MIC (2 mM TU) | MIC (3 mM TU) | MIC (7 mM TU) | MIC (13 mM TU) | MIC (27 mM TU) | MIC (54 mM TU) | MIC (108 mM TU) |
|---|---|---|---|---|---|---|---|---|
| $Au_{101}$TPPMS | 102.4 | 1.6 | 1.6 | 0.8 | 0.8 | 0.8 | 0.8 | 0.8 |
| $Au_{101}$Tre | >282 | 2.2 | 1.1 | 1.1 | 1.1 | 1.1 | 1.1 | 0.6 |
| $Au_{101}$Mal | >344 | 2 | 2.7 | 1.3 | 1.3 | 0.7 | 0.7 | 0.7 |
| AuNP-Citrate | >425 | >425 | >425 | 13 | 1.7 | 1.7 | 1.7 | 0.8 |

Other gold entities tested showed a similar activity profile to $Au_{101}$Mal. The 1.8 nm clusters, $Au_{101}$TPPMS/$Au_{101}$Tre/$Au_{101}$Mal, had better activity compared to 13 nm AuNP-citrate. At lower thiourea concentrations, a slight ligand effect was recorded, with the TPPMS ligand being slightly better than the gold entities having carbohydrate ligands.

Table 5 shows MICs on *P. aeruginosa* PAO1 (μM in [Au]) of $Au_{101}$TPPMS containing different amounts of peracetylated thioglucose ligand, $Ac_4$Glc, vs. the concentration of added TU (mM).

TABLE 5

| Gold entity | MIC (0 mM TU) | MIC (0.05 mM TU) | MIC (0.1 mM TU) | MIC (0.2 mM TU) | MIC (0.4 mM TU) | MIC (1 mM TU) | MIC (2 mM TU) | MIC (3 mM TU) |
|---|---|---|---|---|---|---|---|---|
| $Au_{101}(TPPMS)_{21}Cl_5$ | 102 | 26 | 6.4 | 6.4 | 3.2 | 3.2 | 3.2 | 3.2 |
| $Au_{101}(TPPMS)_{19}(Ac_4Glc)_2Cl_5$ | 141 | 8.8 | 8.8 | 4.4 | 4.4 | 4.4 | 2.2 | 2.2 |
| $Au_{101}(TPPMS)_{11}(Ac_4Glc)_{10}Cl_5$ | 237 | 15 | 7.4 | 7.4 | 3.7 | 1.9 | 1.9 | 1.9 |
| $Au_{101}(TPPMS)_7(Ac_4Glc)_{14}Cl_5$ | 130 | 16 | 16 | 8.1 | 8.1 | 4.1 | 4.1 | 2.1 |

Table 5 shows the effects on MIC of $Au_{101}$TPPMS by incorporating $Ac_4$Glc. The presence of $Ac_4$Glc made the clusters less active at low concentrations of TU. However, as the TU concentrations were increased, these values were comparable to $Au_{101}$TPPMS.

Table 6 shows MICs (μM in [Au]) of different sizes of Au entities vs. the concentration of added TU (mM).

TABLE 6

| Gold entity | MIC (0 mM TU) | MIC (0.2 mM TU) | MIC (0.4 mM TU) | MIC (1 mM TU) | MIC (2 mM TU) | MIC (3 mM TU) | MIC (7 mM TU) |
|---|---|---|---|---|---|---|---|
| [AuTPPMS]Cl | >59 | 59 | 15 | 7.3 | 3.7 | 3.7 | 3.7 |
| $[Au_9(TPPMS)_8]Cl_3$ | >54 | 27 | 13 | 3.4 | 3.4 | 1.7 | 1.7 |
| $Au_{101}(TPPMS)_{21}Cl_5$ | 102 | 6.4 | 3.2 | 3.2 | 1.6 | 1.6 | 0.8 |

To test whether the size of the gold clusters impacts the activity, three sizes of TPPMS-protected Au entities were tested: Au(I) compound, $Au_9$ and the $Au_{101}$ clusters, respectively. The results in Table 6 show that the larger $Au_{101}$ cluster displayed slightly better MICs compared to the smaller cluster $Au_9$ and the Au(I) compound Table 7 shows MICs (μM, [Au]) of several glutathione (GSH)-protected gold nanoclusters against *Pseudomonas aeruginosa* PAO1 in the presence and absence of 7 mM TU.

TABLE 7

| Gold entity | MIC (0 mM TU) | MIC (7 mM TU) | Enhancement |
|---|---|---|---|
| $Au_{18}SG_{14}$ | 147 | <1.1 | >128 |
| $Au_{22}SG_{18}$ | >571 | <1.1 | >512 |
| $Au_{25}SG_{18}$ | >612 | <1.2 | >512 |

To test whether nuclearity and size of thiol-protected gold clusters could affect activation with TU, $Au_{18}$, $Au_{22}$, and $Au_{25}$ glutathione protected clusters were tested with 7 mM TU. The results in Table 7 showed that thiourea improved the activity of all three clusters to <1.2 μM.

Table 8 shows the MICs (μM, [Au]) of Au(I) complexes vs. the concentrations of added TU (mM).

TABLE 8

| Gold entity | MIC (0 mM TU) | MIC (1 mM TU) | MIC (2 mM TU) | MIC (3 mM TU) | MIC (7 mM TU) | MIC (13 mM TU) | MIC (27 mM TU) | MIC (54 mM TU) |
|---|---|---|---|---|---|---|---|---|
| $Au(TU)_2$ | 20.9 | 5.2 | 5.2 | 1.3 | 1.3 | 0.7 | 0.7 | 0.7 |
| $Au(TPPMS)_2$ | >133.2 | 16.6 | 4.2 | 1 | 1 | 1 | 0.3 | 0.3 |
| MS-40 | 5.7 | 5.7 | 5.7 | 5.7 | 5.7 | 2.9 | 2.9 | 1.4 |

The antibacterial activities of all compounds were improved in the presence of TU. The activity of the already active compound MS-40 (trimethylphosphine gold(I) mercaptoethanol) was moderately enhanced (4-fold, at 54 mM TU) compared to the other Au(I) compounds. The activity of $Au(TU)_2$ was enhanced 32-fold while $Au(TPPMS)_2$ showed a >400-fold activity enhancement. These results point to the formation of small Au-thiourea complexes as part (but not all) of the source of antibacterial activity.

Table 9 shows the MICs (μM, [Au]) of the $Au^{3+}$ ion ($HAuCl_4 \cdot 3H_2O$) and the Au(I) drug auranofin on *Pseudomonas aeruginosa* PAO1 with and without TU at 7 mM

TABLE 9

| Gold entity | MIC (0 mM TU) | MIC (7 mM TU) | Enhancement |
|---|---|---|---|
| $HAuCl_4$ ($Au^{3+}$) | 40 | 1.3 | 32 |
| Auranofin | 377 | 1.5 | 256 |

TU also improved the activity of the $Au^{3+}$ ion ($HAuCl_4 \cdot 3H_2O$), inducing a 32-fold change in killing efficiency at 7 mM TU compared to the ion by itself. For the Au(I) drug auranofin, prescribed for inflammation and rheumatoid arthritis, TU at 7 mM enhanced the activity by 256 times Table 10 shows the MICs (μM, [Au]) of $Au_{101}$Glc vs. the concentration of added TU (mM) against *E. coli* ATCC® 25922.

TABLE 10

| Gold entity | MIC (0 mM TU) | MIC (0.2 mM TU) | MIC (0.4 mM TU) | MIC (1 mM TU) | MIC (2 mM TU) | MIC (3 mM TU) | MIC (7 mM TU) | MIC (13 mM TU) |
|---|---|---|---|---|---|---|---|---|
| $Au_{101}Glc$ | >168 | 21 | 21 | 2.6 | 1.3 | 1.3 | 0.7 | 0.7 |

*E. coli* was used to confirm the activity of the combination of gold entities and thiourea on other gram-negative strains. $Au_{101}Glc$ was used in combination with the TU against the *E. coli* wild-type strain ATCC® 25922. The recorded results were similar to those obtained above, showing that the inactive $Au_{101}Glc$ (MIC>168 μM) was rendered very active with the addition of TU (e.g., MIC=0.7 μM at 7 mM [TU]).

Table 11 shows the MICs (μM, [Au]) of gold entities vs. the concentrations of added TU (mM) against methicillin-resistant *Staphylococcus aureus* (MRSA, USA300 JE2).

TABLE 11

| Gold entity | MIC (0 mM TU) | MIC (2 mM TU) | MIC (3 mM TU) | MIC (7 mM TU) | MIC (13 mM TU) | MIC (27 mM TU) | MIC (54 mM TU) | MIC (108 mM TU) |
|---|---|---|---|---|---|---|---|---|
| $Au_{101}Mal$ | >172 | 5.4 | 1.3 | 0.7 | 0.3 | 0.2 | 0.2 | 0.2 |
| $Au_{101}Glc$ | >84 | 5.2 | 2.6 | 0.7 | 0.3 | 0.3 | 0.2 | 0.2 |
| AuNP-Citrate | >53 | >53 | >53 | 0.4 | 0.2 | 0.2 | 0.2 | 0.1 |
| $Au_{101}TPPMS$ | 13 | 1.6 | 0.8 | 0.4 | 0. | 0.2 | 0.2 | 0.2 |
| $Au_{101}Tre$ | >141 | 4.4 | 1.1 | 0.6 | 0.3 | 0.1 | 0.1 | 0.1 |

The broad-spectrum activity of the combination of gold entities and thiourea was furthermore observed on the gram-positive bacterium, methicillin-resistant *Staphylococcus aureus* (MRSA, USA300 JE2). The $Au_{101}$-clusters and the citrate-protected gold nanoparticles all showed remarkable enhancements when used in combination with thiourea. These data were at least 2-fold better compared to the antipseudomonal activities for the corresponding concentrations of TU.

As shown in Table 11, each gold entity in combination with thiourea showed marked improvement in activity compared to the gold entities alone. Above a threshold of 3 mM of TU, the MICs of all the formulations were relatively consistent (0.4-0.7 μM [Au]). This suggests that this concentration of TU is enough to overcome ligand differences of the gold entities.

Table 12 shows the MICs (μM, [Au]) of $Au_{101}TPPMS$ and $Au_{101}Tre$ clusters vs. the concentration of added TU (mM) against *M. smegmatis* $mc^2155$.

TABLE 12

| Gold entity | MIC (0 mM TU) | MIC (0.2 mM TU) | MIC (0.4 mM TU) | MIC (1 mM TU) | MIC (2 mM TU) | MIC (3 mM TU) | MIC (7 mM TU) | MIC (13 mM TU) |
|---|---|---|---|---|---|---|---|---|
| $Au_{101}TPPMS$ | >205 | 102 | 51 | 51 | 13 | 13 | 3.2 | 1.6 |
| $Au_{101}Tre$ | >141 | 141 | 141 | 141 | 71 | 8.8 | 4.4 | 2.2 |

Mycobacteria can be considered a type of gram-positive bacterium but is often categorized as a unique class owing to its much thicker cell wall. $Au_{101}TPPMS$ and $Au_{101}Tre$ were tested on *M. smegmatis* $mc^2155$, a nonvirulent *Mycobacterium* strain related to *M. tuberculosis* that causes TB. Trehalose is a known metabolite of mycobacteria, which allows selective uptake of trehalose-capped nanoparticles by *M. smegmatis.*

As shown in Table 12, the activity of $Au_{101}$TPPMS was higher at low concentrations of TU. However, as the concentration of TU was increased (>3 mM) the activity of the $Au_{101}$Tre was very similar to the phosphine protected cluster. The improvement in the activities of the TU/AuNC system against mycobacteria was lower compared to their activities against *P. aeruginosa* PAO1 and MRSA.

Table 13 shows the MICs (M, [Au]) of gold entities vs. the concentrations of added TU (mM) against *P. aeruginosa* (PAO1), methicillin-resistant *S. aureus* (MRSA), *M. smegmatis* (Smeg), and *E. coli*. For most strains, the maximal effect of TU was reached at 7 mM TU.

TABLE 13

| [TU] | $Au_{101}$TPPMS | | | $Au_{101}$Tre | | | $Au_{101}$Mal | | AuNP-Citrate | | $Au_{101}$Glc | |
|---|---|---|---|---|---|---|---|---|---|---|---|---|
| (mM) | PAO1 | MRSA | *Smeg* | PAO1 | MRSA | *Smeg* | PAO1 | MRSA | PAO1 | MRSA | *E. coli* | MRSA |
| 0 | 102.4 | 13 | >205 | >282 | >141 | >141 | >344 | >172 | >425 | >53 | >168 | >84 |
| 0.2 | | | 102 | | | 141 | | | | | 21 | |
| 0.4 | | | 51 | | | 141 | | | | | 21 | |
| 1 | | | 51 | | | 141 | | | | | 2.6 | |
| 2 | 1.6 | 1.6 | 13 | 2.2 | 4.4 | 71 | 2 | 5.4 | >425 | >53 | 1.3 | 5.2 |
| 3 | 1.6 | 0.8 | 13 | 1.1 | 1.1 | 8.8 | 2.7 | 1.3 | >425 | >53 | 1.3 | 2.6 |
| 7 | 0.8 | 0.4 | 3.2 | 1.1 | 0.6 | 4.4 | 1.3 | 0.7 | 13 | 0.4 | 0.7 | 0.7 |
| 13 | 0.8 | 0.4 | 1.6 | 1.1 | 0.3 | 2.2 | 1.3 | 0.3 | 1.7 | 0.2 | 0.7 | 0.3 |
| 27 | 0.8 | 0.2 | | 1.1 | 0.1 | | 0.7 | 0.2 | 1.7 | 0.2 | | 0.3 |
| 54 | 0.8 | 0.2 | | 1.1 | 0.1 | | 0.7 | 0.2 | 1.7 | 0.2 | | 0.2 |
| 108 | 0.8 | 0.2 | | 0.6 | 0.1 | | 0.7 | 0.2 | 0.8 | 0.1 | | 0.2 |

Table 14 shows the MICs (M [Au] and minimum bactericidal concentration (MBC (μM, [Au])) in parenthesis) of $Au_{101}$Mal with 7 mM of TU (mM) against different strains of bacteria including Gram-negative, Gram-positive and mycobacteria strains

TABLE 14

| Bacteria strains | MIC (MBC)[a] |
|---|---|
| Gram-negative | |
| *P. aeruginosa* (PAO1) | 1.4/2.7 (5.4) |
| *P. aeruginosa* (ATCC 27853) | 1.4/2.7 (5.4) |
| *E. coli* (ATCC 15597) | 11 (11) |
| *E. coli* (ATCC 25922) | 5.4 (11) |
| *E. coli* (ATCC 33456) | 1.4/2.7 (5.4) |
| *E. coli* (BORT WT)[b] | 1.4/2.7 (11) |
| *E. coli* (BORT CIP) | 1.4 (5.4) |
| *K. pneumoniae* (B5055 (O1:K2)) | 2.7 (5.4) |
| *A. baumannii* (ATCC 19606) | 5.4 (43) |
| Gram-positive | |
| *S. aureus* JE2 (USA300) | 1.4 (1.4) |
| *S. aureus* (ATCC 29213) | 0.7 (1.4) |
| *S. epidermidis* (ATCC 35984) | 0.4 (1.4) |
| Mycobacteria | |
| *M. smegmatis* ($mc^2$155) | 2.7/5.4 (11) |
| *M. smegmatis* ($mc^2$651)[c] | 2.7/5.4 (11) |

[a]All tests were repeated twice. In cases where the two repeats were identical, only one data is presented.
[b]Ciprofloxacin-resistant strain of BORT.
[c]Isoniazid-resistant strain of $mc^2$155

The combination of $Au_{101}$Mal with 7 mM TU had broad spectrum activity against gram negative, gram positive and Mycobacteria strains including strains that were resistant to antibiotics.

Table 15 shows the MICs (μM, [Au]) and minimum bactericidal concentration (MBC (μM, [Au])) in parenthesis of $Au_{101}$Mal with 7 mM of TU (mM) against clinical isolates of *P. aeruginosa* possessing multidrug resistance (MDR).

TABLE 15

| Strain†+ | MIC (MBC) | Multi-drug resistance*+ | Resistance mechanisms+ |
|---|---|---|---|
| 229 | 1.4/1.4 (5.4) | AZT, CEF, CED, CED/AVI, CIP, DOR, IMI, LEV, MER, PIP/TAZ | OXA-50, PAO |
| 231 | 1.4/2.7 (5.4) | AZT, CEF, CED, CIP, DOR, GEN, IMI, LEV, MER, PIP, TOB | aac(6')-IIc, KPC-5, OXA-2, OXA-50, PAO |
| 232 | 0.7/1.4 (5.4) | CIP, GEN, IMI, LEV, TOB | aadA6, OXA-50, PAO, strA, strB, sul1, tet(C) |
| 235 | 1.4/2.7 (5.4) | AMI, AZT, CF, CED, CED/AVI, CEZ/TAZ, CIP, COL, DOR, GEN, IMI, LEV, MER, PIP/TAZ, TOB | aadB, OXA-10, OXA-50, PAO, sull, VEB-1 |
| 236 | 0.7/1.4 (5.4) | CIP, GEN, IMI, LEV, TOB | aadB, aph(3')-IIb, OXA-50, PAO |
| 239 | 0.7/1.4 (5.4) | AMI, AZT, CEF, CED, CED/AVI, CEZ/TAZ, CIP, COL, DOR, GEN, IMI, LEV, MER, PIP/TAZ, TOB | aac(6')-IIa, aadB, aph(3')-Ic, cmlA1, dfrB5, GES-1, OXA-10, OXA-50, strA, strB, tet(G), VIM-11 |
| 241 | 0.7/1.4 (5.4) | AZT, CEF, CED, CED/AVI, CEZ/TAZ, CIP, DOR, GEN, IMI, LEV, MER, PIP/TAZ, TOB | aac(6')-IIc, aadA7, catB7, IMP-1, OXA-101, OXA-50, OXA-9, PAO, sul1 |
| 245 | 0.7/1.4 (5.4) | AMI, AZT, CEF, CED, CED/AVI, CEZ/TAZ, CIP, DOR, IMI, LEV, MER, TOB | aph(3'), OXA, PAO, sul1, VIM-2 |
| 246 | 0.7/1.4 (5.4) | AMI, AZT, CEF, CED, CED/AVI, CEZ/TAZ, CIP, DOR, GEN, IMI, LEV, MER, PIP/TAZ, TOB | aadB, NDM-1, OXA-10, OXA-50, PAO, rmtD2, tet(G), VEB-1 |
| 249 | 1.4/1.4 (5.4) | AMI, AZT, CEF, CED, CED/AVI, CEZ/TAZ, CIP, DOR, GEN, IMI, LEV, MER, PIP/TAZ, TOB | aac(3)-Id, aadA2, cmlA1, dfrB5, OXA-4, OXA-50, PAO, tet(G), VIM-2 |
| 252 | 1.4/1.4 (5.4) | AZT, CEF, CED, CIP, DOR, LEV, MER, PIP/TAZ | aadA1, aadA6, OXA-2, OXA-50, PAO, sul1 |
| 268 | 0.7/1.4 (5.4) | AZT, CEF, CED, CIP, DOR, IMI, LEV, MER, PIP/TAZ | catB7, OXA-50, PAO |
| 767 | 0.7/1.4 (5.4) | AMI, AZT, DEF, CED, CED/AVI, CEZ/TAZ, CIP, DOR, GEN, IMI, LEV, MER, PIP/TAZ, TOB | GES-20 |
| 768 | 1.4/1.4 (5.4) | AMI, AZT, CEF, CED, CED/AVI, CEZ/TAZ, CIP, COL, DOR, GEN, IMI, LEV, MER, PIP/TAZ, TOB | GES-19, GES-20 |
| 770 | 1.4/1.4 (5.4) | AMI, AZT, CEF, CED, CED/AVI, CEZ/TAZ, CIP, DOR, GEN, IMI, LEV, MER, PIP/TAZ, TOB | GES-19, GES-26 |

†CDC Strain number

*AMI amikacin, AZT aztreonam, CEF cefepime, CED ceftazidime, AVI avibactam, CEZ ceftolozane, TAZ tazobactam, CIP ciprofloxacin, COL colistin, DOR doripenem, GEN gentamicin, IMI imipenem, LEV levofloxacin, MER meropenem, PIP piperacillin, TOB tobramycin +Data provided by the CDC. aac(3)-Id aminoglycoside resistance, aac(6')-Iia aminoglycoside resistance, aac(6')-Ilc aminoglycoside resistance (aminoglycoside 6'-N-acetyltransferase), aadA1 aminoglycoside resistance, aadA2 aminoglycoside resistance, aadA6 aminoglycoside adenylyltransferase AADA6, aadA7 Aminoglycoside resistance, aadB aminoglycoside resistance (aminoglycoside-2"-adenylyltransferase), aph (3')-Ic aminoglycoside resistance (neomycin phosphotransferase), aph(3')-Iib aminoglycoside resistance (aminoglycoside phosphotransferase (3')IIps), catB7 phenicol resistance (chloramphenicol acetyltransferase), cmlAl phenicol resistance chloramphenicol resistance, dfrB5 trimethoprim resistance (dihydrofolate reductase), GES-1 beta-lactam resistance (extended-spectrum beta-lactam GES-7), IMP-1 beta-lactam resistance (metallo-beta-lactamase IMP-l-like), KPC-5 beta-lactamase KPC-5, NDM-1 beta-lactam resistance (metallo-beta-lactamase), OXA-10 beta-lactam resistance, OXA-2 beta-lactam resistance oxacillinase type 2, OXA-4 beta-lactam resistance (beta-lactamase OXA-4), OXA-50 beta-lactam resistance (oxacillinase), OXA-9 beta-lactam resistance (oxacillinase-carbenicillinase), PAO beta-lactam resistance (a beta-lactamase precursor), strA aminoglycoside 3"-phosphotransferase, strB streptomycin phosphotransferase, sull sulphonamide resistance dihydropteroate synthase protein Sull, tet(C) tetracycline resistance, tet(G) tetracycline resistance protein, tet(G) tetracycline resistance, VEB-1 beta-lactam resistance extended-spectrum beta-lactamase, VIM-11 beta-lactam resistance, VIM-2 metallo-beta-lactamase.

Figure 3A:
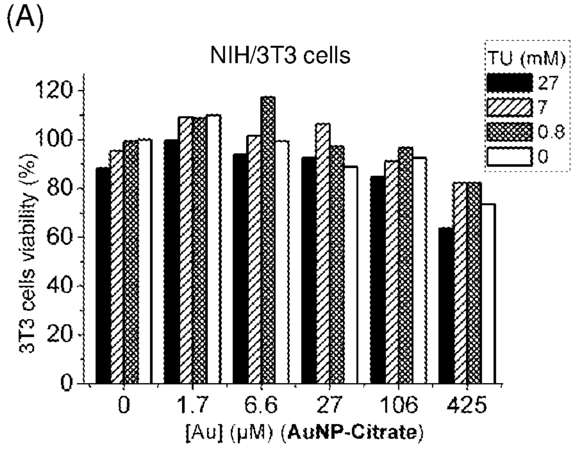
FIGS. 3A-3B show the viability of NIH/3T3 cells (FIG. 3A) and A549 cells (FIG. 3B), treated with a combination of different concentrations of TU and 13 nm AuNP-citrate, in which the Au concentrations were quantitated by ICP-MS.
Figure 3B:
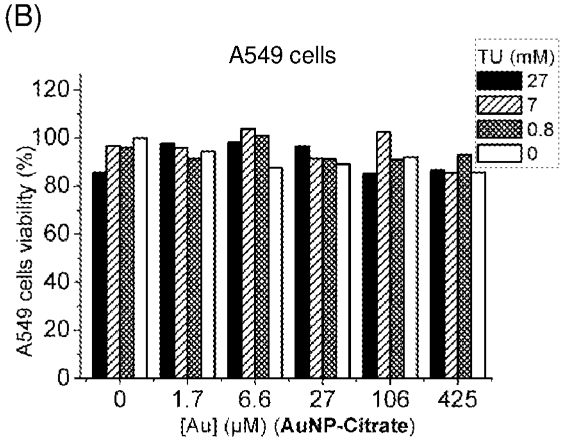
Figure 4A:
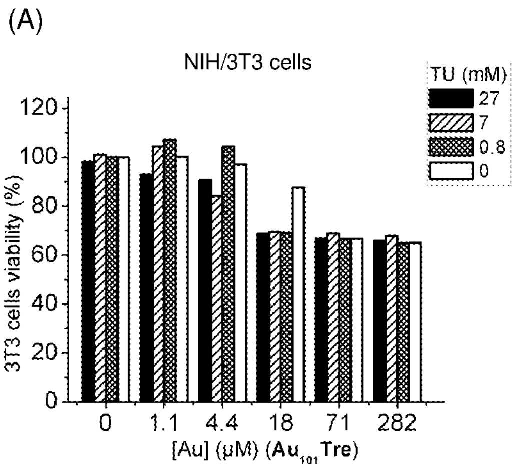
FIGS. 4A-4B show the viability of NIH/3T3 cells (FIG. 4A) and A549 cells (FIG. 4B), treated with a combination of different concentrations of TU and $Au_{101}$Tre, in which the Au concentrations were quantitated by ICP-MS.
Figure 4B:
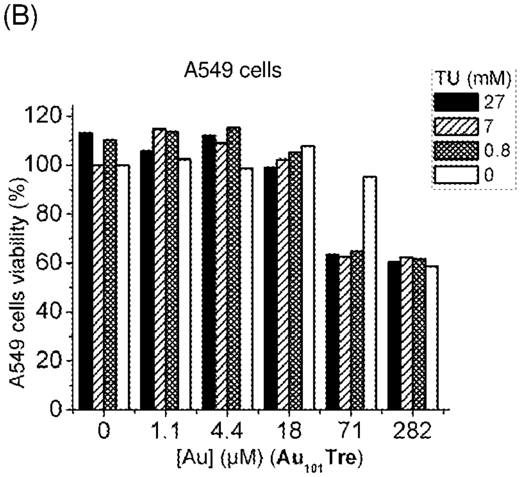
Figure 5A:
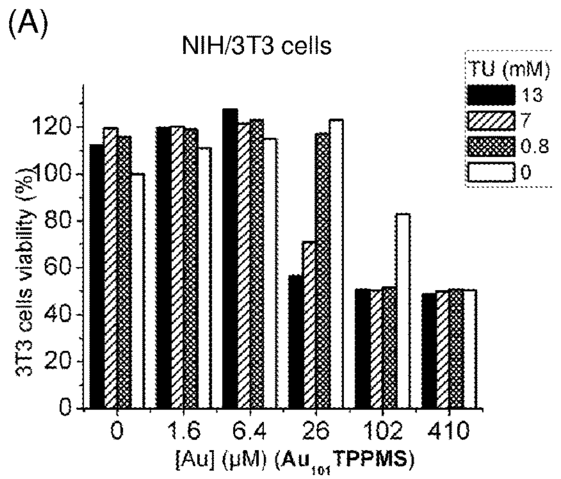
FIGS. 5A-5B show the viability of NIH/3T3 cells (FIG. 5A) and A549 cells (FIG. 5B), treated with a combination of different concentrations of TU and 1.8 nm gold nanoclusters protected with triphenylphosphine-3-sulfonate ($Au_{101}$TPPMS), in which the Au concentrations were quantitated by ICP-MS.
Figure 5B:
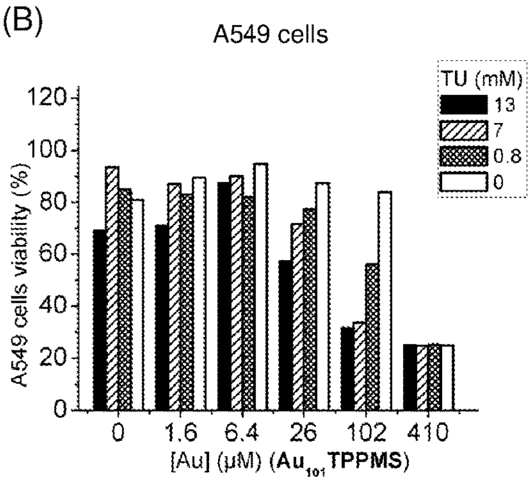
Figure 6A:
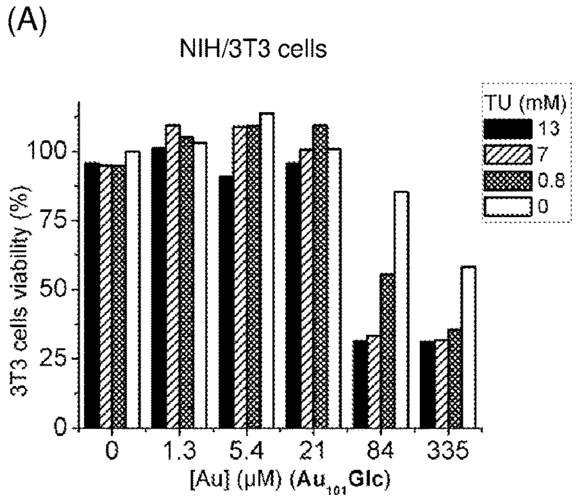
FIGS. 6A-6B show the viability of NIH/3T3 cells (FIG. 5A) and A549 cells (FIG. 5B), treated with a combination of different concentrations of TU and 1.8 nm gold nanoclusters protected with D-glucose ($Au_{101}$Glc), in which the Au concentrations were quantitated by ICP-MS.
Figure 6B:
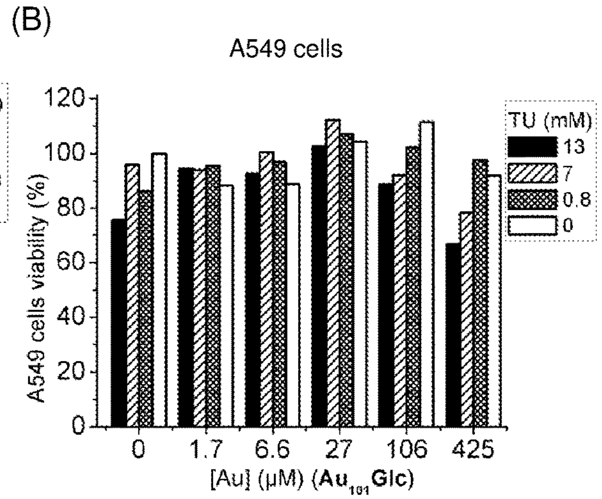

$Au_{101}$Mal with TU (7 mM) was active against multidrug resistant (MDR) strains of *P. aeruginosa* isolated from patients. These strains have extensive resistant mechanisms against conventional antibiotics including the last-resort drug, colistin. $Au_{101}$Mal with 7 mM TU was bactericidal against all tested strains at <5.4 μM The cytotoxicity of AuNP-Citrate, $Au_{101}$Tre, $Au_{101}$TPPMS and $Au_{101}$Glc was evaluated on A549 and NIH/3T3 cells. AuNP-Citrate showed the lowest degree of toxicity to either cell line. The AuNP-Citrate displayed >80% viability even with high concentrations of Au (106 μM for NIH/3T3 (FIG. 3A) and 425 μM for A549 (FIG. 3B)) combined with the highest amount of added TU (27 mM) in the assay.

The general trend of the other gold entities depended more on the independent gold entity toxicity than the inclusion of thiourea. Therefore, the observed convergence of toxicity that is observed with increase in TU in antibacterial assays is not as emergent in mammalian cells. This allows for selectivity in the design of the nanostructures to maximize the antibacterial activity and minimize the cytotoxicity.

Table 16 shows MICs of gold entities against bacteria, $CC_{50}$ values of gold entities against A549 or 3T3/NIH cells (at TU=7 mM), and the selectivity indices (S.I.=$CC_{50}$/MIC).

TABLE 16

| Bacterium | Gold entity | MIC (μM) | 3T3 cells CC$_{50}$ (μM) | 3T3 cells S.I. | A549 cells CC$_{50}$ (μM) | A549 cells S.I. |
|---|---|---|---|---|---|---|
| PAO1 | $Au_{101}$TPPMS | 0.8 | 26 | 32 | 102 | 128 |
| | $Au_{101}$Tre | 1.1 | >283 | >256 | >283 | >256 |
| | $Au_{101}$Mal | 1.3 | >345 | >256 | >345 | >256 |
| | AuNP-Citrate | 13 | >425 | >32 | >425 | >32 |
| MRSA | $Au_{101}$TPPMS | 0.4 | 26 | 64 | 102 | 256 |
| | $Au_{101}$Tre | 0.6 | >283 | >512 | >283 | >512 |
| | $Au_{101}$Mal | 0.7 | >345 | >512 | >345 | >512 |
| | AuNP-Citrate | 0.4 | >425 | >1024 | >425 | >1024 |
| | $Au_{101}$Glc | 0.7 | 42 | 64 | >335 | >512 |
| *Smeg.* | $Au_{101}$TPPMS | 3.2 | 26 | 8 | 102 | 32 |
| | $Au_{101}$Tre | 4.4 | >283 | >64 | >283 | >64 |
| *E. coli* | $Au_{101}$Glc | 0.7 | 42 | 64 | >335 | >512 |

The combination of gold entities with thiourea can be a powerful broad-spectrum antibiotic. AuNP-Citrate, $Au_{101}$Tre, $Au_{101}$TPPMS and $Au_{101}$Glc showed sub-μM activity of Au while maintaining low toxicity to mammalian cells. The selectivity index (S.I.), a value that ratios the MIC of a drug and the concentration that is cytotoxic to 50% of the cells (CC$_{50}$), is a measure of the preferential killing of bacteria over mammalian cells. The higher the S.I., the safer and better the therapeutic potential of the drug.

The S.I. data at a fixed concentration of 7 mM of TU are presented in Table 11. These data demonstrate that TU could potentiate the antimicrobial activities of all AuNPs, of which the nontoxic carbohydrate and AuNP-Citrate showed more than 2-3 orders of magnitude increase in antimicrobial activities while maintaining low cytotoxicities toward mammalian cells.

Figure 7A:
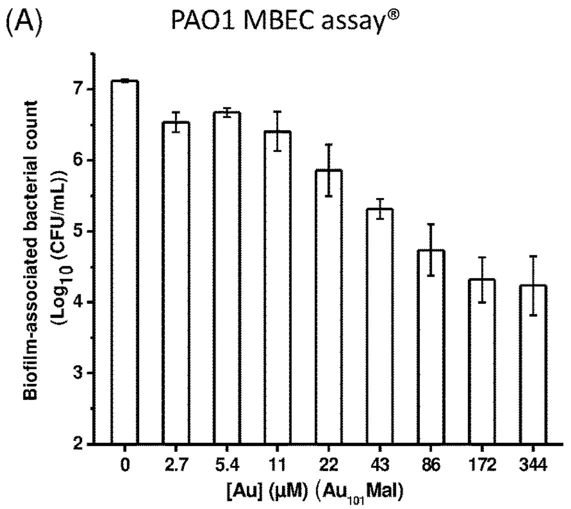
FIGS. 7A-7B show the survival of *P. aeruginosa* PAO1 biofilms as bacterial counts from the MBEC Assay® (FIG. 7A) and as $OD_{595}$ by crystal violet staining (FIG. 7B), treated with a combination of TU (7 mM) and 1.8 nm gold nanoclusters protected with D-maltose ($Au_{101}$Mal), in which the Au concentrations were quantitated by ICP-MS.
Figure 7B:
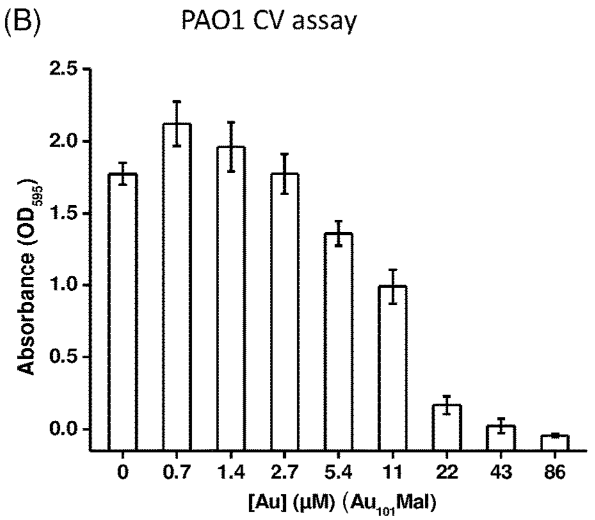
Figure 8A:
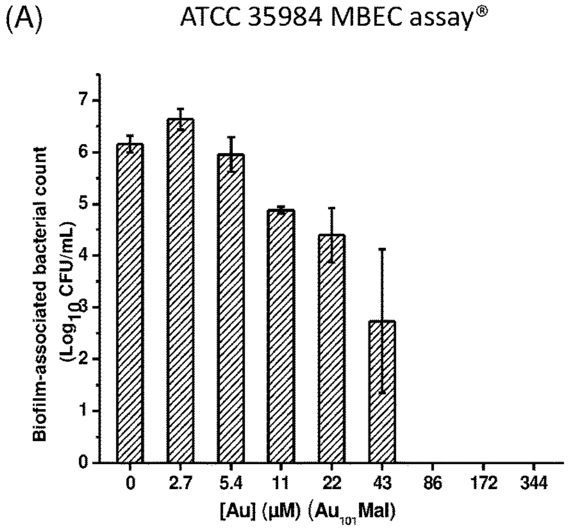
FIGS. 8A-8B show the survival of *S. epidermidis* ATCC 35984 biofilms using bacterial counts from the MBEC Assay® (FIG. 8A) and as $OD_{595}$ by crystal violet staining (FIG. 8B), treated with a combination of TU (7 mM) and 1.8 nm gold nanoclusters protected with D-maltose.
Figure 8B:
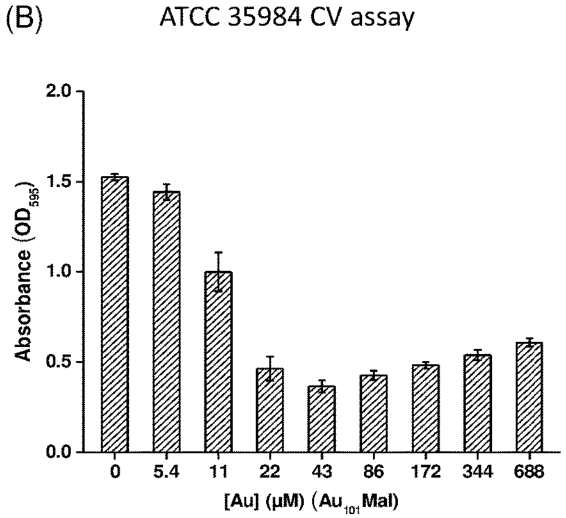

The ability of a combination of gold entities with TU (7 mM) to removal biofilm was also investigated on Gram-negative (*Pseudomonas aeruginosa* PAO1, FIGS. 7A-7B) and Gram-positive (*Staphylococcus epidermidis* ATCC 35984, FIGS. 8A-8B). $Au_{101}$Mal with 7 mM of TU reduced the number of bacteria associated with *P. aeruginosa* PAO1 biofilms (FIG. 7A) and eliminated the biofilm mass (FIG. 7B). $Au_{101}$Mal with 7 mM of TU eradicated *S. epidermidis* ATCC 35984 biofilm from the MBEC Assay® (FIG. 8A) and eliminated biofilm mass using the crystal violet (CV) assay (8B).

Figure 9:
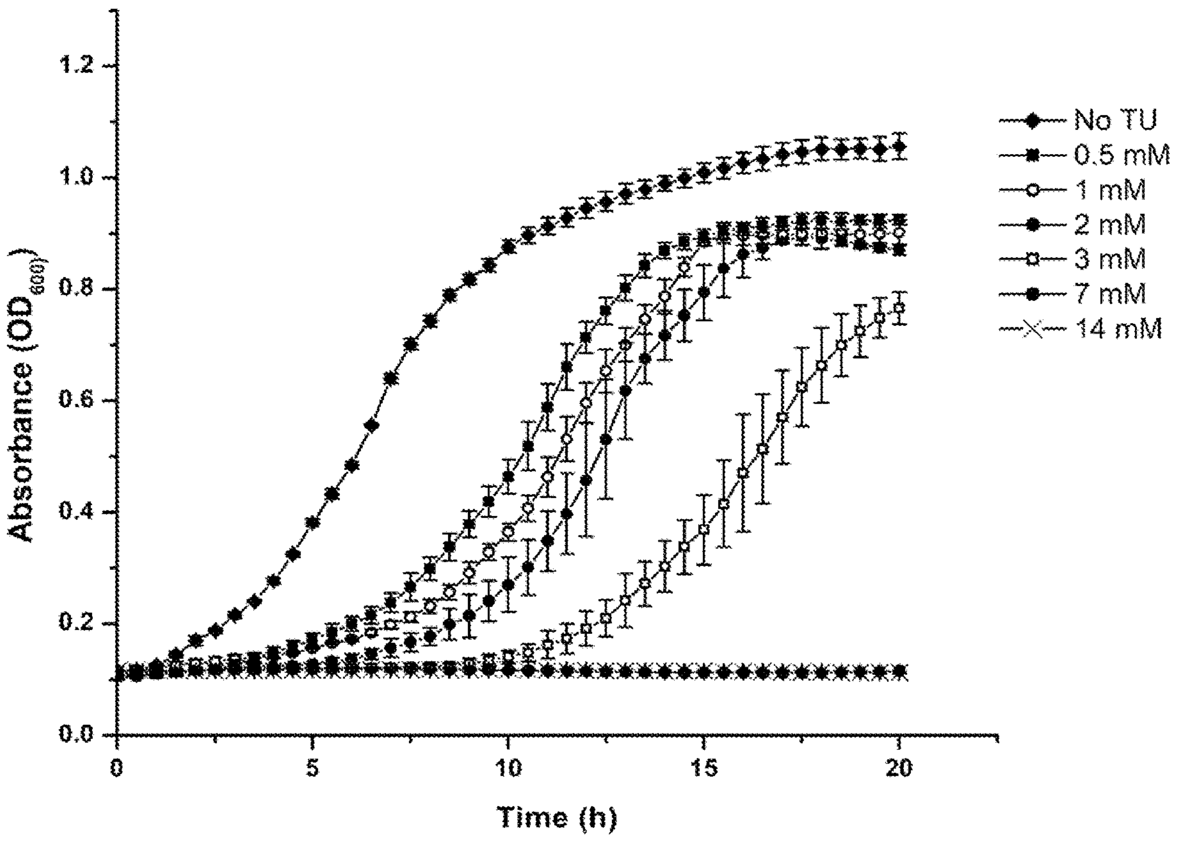
FIG. 9 shows the growth curve of *P. aeruginosa* PAO1 as measured by absorbance ($OD_{600}$) after internalization of $Au_{101}$Mal and exposure to different concentrations of TU.

TU also showed capability of intracellular activation. $Au_{101}$Mal incubated with *P. aeruginosa* PAO1 which was then washed several times to ensure removal of extracellular $Au_{101}$Mal. Serial dilutions of TU were then added to the bacteria and incubated for 20 h. Monitoring the bacteria growth using OD$_{600}$ (FIG. 9) showed that the addition of TU slowed down the bacteria growth even at low concentration (0.5 mM), and at >7 mM, completely inhibited bacteria growth.

What is claimed is:

1. A composition comprising: a metal entity and an activating agent, or pharmaceutically acceptable salts thereof, wherein:

the composition comprises a synergistic amount of the activating agent and the metal entity;

the activating agent comprises thiourea; and the metal entity comprises at least one of auranofin, gold nanoclusters, or a combination thereof, wherein the gold nanoclusters comprise at least one of $Au_{101}$Mal, $Au_{101}$Tre, $Au_{101}$Glc, AuCitrate, $Au_{18}SG_{14}$, $Au_{22}SG_{18}$, $Au_{25}SG_{18}$, $Au_{101}$TPPMS, Au(TPPMS)$_2$, [AuTPPMS]Cl, [$Au_9$(TPPMS)$_8$]$Cl_3$, $Au_{101}$(TPPMS)$_{21}Cl_5$, HAu$Cl_4$($Au^{3+}$), $Au_{101}$(TPPMS)$_{19}$($Ac_4$Glc)$_2Cl_5$, $Au_{101}$(TPPMS)$_{14}$($Ac_4$Glc)$_7Cl_5$, $Au_{101}$(TPPMS)$_{11}$($Ac_4$Glc)$_{10}C_{15}$, $Au_{101}$(TPPMS)$_7$($Ac_4$Glc)$_{14}Cl_5$, or a combination thereof.

2. The composition of claim 1, wherein the gold nanoclusters comprise an average diameter of up to 3 nm, the gold nanoclusters comprise an average diameter of greater than 3 nm, or a combination thereof.

3. The composition of claim 1, wherein the gold nanoclusters comprise at least one of $Au_{101}$Mal, $Au_{101}$Tre, $Au_{101}$Glc, AuCitrate, $Au_{18}SG_{14}$, $Au_{22}SG_{18}$, $Au_{25}SG_{18}$, $Au_{101}$TPPMS, Au(TPPMS)$_2$, [AuTPPMS]Cl, [$Au_9$(TPPMS)$_8$]$Cl_3$, $Au_{101}$(TPPMS)$_{21}Cl_5$, HAu$Cl_4$($Au^{3+}$), $Au_{101}$(TPPMS)$_{19}$($Ac_4$Glc)$_2Cl_5$, $Au_{101}$(TPPMS)$_{14}$($Ac_4$Glc)$_7Cl_5$, $Au_{101}$(TPPMS)$_{11}$($Ac_4$Glc)$_{10}Cl_5$, $Au_{101}$(TPPMS)$_7$($Ac_4$Glc)$_{14}Cl_5$, or a combination thereof.

4. The composition of claim 1, wherein the gold nanoclusters comprise at least one of $Au_{101}$Mal, $Au_{101}$Tre, $Au_{101}$Glc, or a combination thereof.

5. The composition of claim 1, wherein the gold nanoclusters comprise AuCitrate.

6. The composition of claim 1, wherein the metal entity comprises auranofin.

7. The composition of claim 1, further comprising a pharmaceutically acceptable carrier.

8. The composition of claim 1, wherein the gold nanoclusters comprise at least one of $Au_{18}SG_{14}$, $Au_{22}SG_{18}$, $Au_{25}SG_{18}$, or a combination thereof.

9. The composition of claim 1, wherein the gold nanoclusters comprise at least one of [$Au_9$(TPPMS)$_8$]$Cl_3$, $Au_{101}$(TPPMS)$_{21}Cl_5$, or a combination thereof.

10. The composition of claim 1, wherein the gold nanoclusters comprise at least one of $Au_{101}$(TPPMS)$_{19}$($Ac_4$Glc-S)$_2Cl_5$, $Au_{101}$(TPPMS)$_{14}$($Ac_4$Glc-S)$_7Cl_5$, $Au_{101}$(TPPMS)$_{11}$($Ac_4$Glc-S)$_{10}Cl_5$, $Au_{101}$(TPPMS)$_7$($Ac_4$Glc-S)$_{14}Cl_5$ or a combination thereof.

11. A composition comprising:

an activating agent that comprises a thiourea; and a metal compound comprising auranofin or gold nanoclusters, wherein the gold nanoclusters comprise $Au_{101}$Mal, $Au_{101}$Tre, $Au_{101}$Glc, AuCitrate, $Au_{18}SG_{14}$, $Au_{22}SG_{18}$, $Au_{25}SG_{18}$, $Au_{101}$TPPMS, Au(TPPMS)$_2$, [AuTPPMS]Cl, [$Au_9$(TPPMS)$_8$]$Cl_3$, $Au_{101}$(TPPMS)$_{21}Cl_5$, HAu$Cl_4$($Au^{3+}$), $Au_{101}$(TPPMS)$_{19}$($Ac_4$Glc)$_2Cl_5$, $Au_{101}$(TPPMS)$_{14}$($Ac_4$Glc)$_7Cl_5$, $Au_{101}$(TPPMS)$_{11}$($Ac_4$Glc)$_{10}Cl_5$, or $Au_{101}$(TPPMS)$_7$($Ac_4$Glc)$_{14}Cl_5$, wherein the composition comprises a synergistic amount of the activating agent and the metal compound.

12. A method of treating a bacterial infection in a patient comprising administering a therapeutically effective amount of a composition according to claim 1.

13. The method of claim 12, wherein the bacterial infection is caused by a gram-negative bacterium, a gram-positive bacterium, an ESKAPE pathogen, *Escherichia* sp., mycobacteria, *Pseudomonas* sp., *Burkholderia* sp., *Helicobacter* sp., *Borrelia* sp., or a combination thereof;

the method further comprises administering a therapeutically effective amount of an antibacterial agent;

or a combination thereof.

14. A method of inhibiting the growth of a bacterium in vitro or in vivo comprising contacting a bacterium, virus, parasite, fungus, protozoa, or worm with a composition according to claim 1.

15. The method of claim 14, wherein the bacterium is a gram-negative bacterium, a gram-positive bacterium, *mycobacterium*, ESKAPE pathogen, *Escherichia* sp., *Escherichia coli, Pseudomonas* sp., *Helicobacter* sp., *Burkholderia* sp., *Borrelia* sp., or a combination thereof;

the method further comprises administering a therapeutically effective amount of an antibacterial agent;

or a combination hereof.

16. The method of claim 14, wherein contacting the bacterium with the composition comprises administering a therapeutically effective amount of the composition to a patient with a biofilm infection, wherein the composition is effective at treating the biofilm infection.

17. The method of claim 14, wherein contacting the bacterium with the composition comprises contacting a biofilm with the composition in vitro or in vivo, wherein the composition is effective at inhibiting the growth of the biofilm.

* * * * *